United States Patent [19]

Wikstrom et al.

[11] Patent Number: 5,461,061

[45] Date of Patent: Oct. 24, 1995

[54] CENTRALLY ACTING 6,7,8,9-TETRAHYDRO-3H-BENZ (E) INDOLE HETEROCYCLICS

[76] Inventors: Hakan V. Wikstrom, Elsscholtleen 32, NL-9721 WN Groningen, Netherlands; Per A. E. Carlsson, Torid Wulffsgatan 50, S-413 19 Goteborg, Sweden; Bengt R. Andersson, Lungmansgatan 31E/5, 413 11 Goteborg, Sweden; Kjell A. I. Svensson, Viktoriagatan 15, S-41125 Goteborg, Sweden; Stig T. Elebring, Dalhemsgatan 8 B, S-431 37 Molndal, Sweden; Nils P. Stjernlof, Skrattmisgangen 44, 421 69 Vastra Frolunda, Sweden; Arthur G. Romero, 2721 Lake Chevy Chase Dr., Kalamazoo, Mich. 49008; Susanne R. Haadsma-Svensson, Viktoriagatan 15, S-41125 Goteborg, Sweden; Chiu-Hong Lin, 3720 Pinetree; Michael D. Ennis, 2416 Deep Forest Ct., both of Portage, Mich. 49002

[21] Appl. No.: 144,857

[22] Filed: Oct. 28, 1993

Related U.S. Application Data

[62] Division of Ser. No. 907,932, Jul. 1, 1992, Pat. No. 5,288, 748 which is a continuation-in-part of PCT/US91/00018, Jan. 8, 1991, which is a continuation-in-part of Ser. No. 464,126, Jan. 11, 1990, abandoned.

[51] Int. Cl.$^6$ .................................................. A61K 31/475
[52] U.S. Cl. ................................................ 514/292; 546/84
[58] Field of Search ................................. 514/292; 546/84

[56] References Cited

U.S. PATENT DOCUMENTS

| | | |
|---|---|---|
| 4,060,626 | 11/1977 | Hrstka et al. . |
| 4,370,341 | 1/1983 | Asselin et al. ........................ 548/427 |
| 4,510,157 | 4/1985 | Asselin et al. ........................ 548/427 |
| 4,564,613 | 1/1986 | Boltze et al. ........................... 546/84 |
| 4,959,479 | 9/1990 | Nagawa .................................. 548/427 |
| 5,061,711 | 10/1991 | Urakami et al. ....................... 514/292 |

FOREIGN PATENT DOCUMENTS

| | | |
|---|---|---|
| 2740836 | 9/1977 | Germany . |
| 48-30078 | 9/1973 | Japan ..................................... 546/84 |
| 91-00856 | 1/1991 | WIPO .................................... 548/427 |
| 91-11435 | 6/1991 | WIPO .................................... 548/430 |

OTHER PUBLICATIONS

Wilkstrom et al. Chem. Abstr. vol. 115 entry 23076a abstracting PCT 90–11435 (1991).

Shagalov, L. B. et al., "Benzindoles, 17. Vilsmeier reaction in angular tetrahydrobenzindoles," Chem. Abstr. 91:56747v (1979).

Shagalov, L. B. et al., "Benzindoles, XIV. Synthesis of angular tetrahydro[4,5]- and [6,7]benzindoles," Chem. Abstr. 89:146703lr (1978).

Asselin, A. A. et al., "Drug Design via Pharmacophore Identification. Dopaminergic Activity of 3H-Benz[e] indol-8-amines and Their Mode of Interaction with the Dopamine Receptor," J. Med. Chem. 29-648–54 (1986).

Wikstrom, H. et al., "Resolved 6,7,8,9-Tetrahydro-N, N-dimethyl-3H-benz[e]indol-8-amine: Central Dopamine and Serotonin Receptor Stimulating Properties," J. Med. Chem. 32:2273–76 (1989).

Nichols, D. E. et al., "Synthesis and Evaluation of N,N-Di-n-propyltetrahydrobenz[f]indol-7-amine and Related Congeners as Dopaminergic Agonists," J. Med. Chem. 32:2128–34 (1989).

*Primary Examiner*—Donald G. Daus
*Attorney, Agent, or Firm*—Donald L. Corneglio

[57] ABSTRACT

A compound of Formula I or pharmaceutically acceptable salts of Formula I, where $R^1$ is H, $C_1$–$C_3$ alkyl, —$(CH_2)_n CONH_2$ where n is 2 to 6, $(CH2)_n$-1-(4,4-dimethylpiperidine-2,6-dione-yl), or cyclopropylmethyl;

$R^2$ is hydrogen, $C_1$–$C_8$ alkyl, $C_3$–$C_8$ cycloalkyl or combined with $R^1$ to form a $C_3$–$C_8$ cycloalkyl, $C_2$–$C_8$ alkenyl, $C_2$–$C_8$ akynyl, $(CH_2)_n$—X—Ar where X is O, S, or NH, 3,3,3-trifluoropropyl, —$(CH_2)_m$—$R^9$ where m is 2 or 3 and $R^9$ is phenyl, 2-thiophenyl or 3-thiophenyl; $R^3$ is hydrogen, $C_1$–$C_3$ alkyl, 2,2,2-trifluoroethyl, 3,3,3-trifluoropropyl, formyl, CN, halogen, $CH_2 OR^2$, $C(O)C(O)OR^1$, $C(O)CO$ $NR^1R^2$, —$(CH_2)_q$—$NR^1R^2$ where q is 0 to 5, C=$NOR^2$, 2(4,5-dihydro)oxazolyl, or $COR^{10}$ where $R^{10}$ is H, $R^1$, $NR^1R^2$ or $CF_3$; $R^4$ is hydrogen, $C_1$–$C_3$ alkyl, cyclopropylmethyl, $CF_3$, 2,2,2-trifluoroethyl, CN, $CONR^1R^2$, =O, 2(4,5-dihydro)imidazolyl, 2(4,5-dihydro)oxazolyl, 2-oxazolyl, 3-oxadiazolyl, or 3,3,3-trifluoropropyl; $R^5$ is hydrogen, $R^1$, $OCH_3$, $C(O)CH_3$ or $C(O)OR^1$; X is (a) a valence bond, (b) $CH_2$, or (c) O, S or $NR^5$ where $R^5$ is H, $C_1$–$C_8$ alkyl, $C_3$–$C_8$ cycloalkyl, benzyl, $COR^6$ where $R^6$ is a $C_1$–$C_3$ alkyl, phenyl, or $CONR^7R^8$ where $R^7$ and $R^8$ are independently H or $C_1$–$C_3$ alkyl; and Z is a hydrogen or halogen;

provided that when X is $CH_2$, at least one of $R_3$ and $R_4$ is other than hydrogen or $C_1$–$C_3$ alkyl. The compounds of Formula I are suitable for treating disorders of the central nervous system, particularly as 5-$HT_{1A}$ receptor agonists.

12 Claims, No Drawings

CENTRALLY ACTING 6,7,8,9-TETRAHYDRO-3H-BENZ (E) INDOLE HETEROCYCLICS

CROSS-REFERENCE TO RELATED PATENT APPLICATIONS

This application is a divisional of U.S. Ser. No. 07/907,932, filed Jul. 1, 1992, U.S. Pat. No. 5,288,784 which is a continuation-in-part of PCT International Application No. PCT/US91/00018, filed Jan. 8, 1991; which, in turn, is a continuation-in-part of U.S. Ser. No. 07/464,126, filed Jan. 11, 1990, abandoned.

FIELD OF INVENTION

The present invention is directed toward 6,7,8,9-tetrahydro-N,N-dialkyl-8-amino3H-benz(e)indoles and their pharmaceutically acceptable salts. Pharmaceutical preparations of these compounds are useful for central nervous system disorders such as for a therapeutic effect on $5\text{-HT}_{1A}$ receptors in mammals.

BACKGROUND OF THE INVENTION

Evidence from depressed patients indicates that the neurotransmission in the central nervous system (CNS) may be disturbed. These disturbances involve the neurotransmitters norepinephrine (NE) and 5-hydroxytryptamine (5-HT). The drugs most frequently used in the treatment of depression are considered to act by improving the neurotransmission of either or both of these physiological agents. The mechanism of action for conventional drugs used to treat mental depression is generally believed to be indirect. It is thought the drugs block the re-uptake of the neurotransmitters released from nerve terminals in the CNS, NE and/or 5-HT, which increases the concentration of these transmitters in the synaptic cleft and restores an adequate neurotransmission. For example, the clinically documented antidepression drug, zimelidine (dimethylamino-1-(4-bromo-phenyl)-1-(3-pyridyl)propene) acts as such a re-uptake inhibitor with high selectivity for 5-HT neurons.

Available data suggests that the enhancement of 5-HT neurotransmission will primarily improve depressed mood and anxiety, whereas the enhancement of norepinephrine neurotransmission will improve retardation symptoms occurring in depressed patients. In recent years many efforts have been made to develop new drugs with high selectivity for the improvement of the 5-HT neurotransmission in the CNS.

A fundamentally different way to improve the neurotransmission in the central 5-HT neurons would be to use a 5-HT receptor agonist acting directly upon the 5-HT receptors, particularly the $5\text{-HT}_{1A}$ receptor. In order to minimize undesired side effects, a high selectivity for this kind of receptor would be necessary.

Clinically, $5\text{-HT}_{1A}$ agonists have also demonstrated anxiolytic properties. The drug, Buspirone hydrochloride is the only currently available marketed $5\text{-HT}_{1A}$ agonist having anxiolytic activity. This compound antagonizes dopamine receptors at the same dose it stimulates $5\text{-HT}_{1A}$ receptors. A similar drug, gepirone also has dopamine antagonist properties. These dopamine antagonist properties reduce the clinical utility of these compounds because long term treatment with dopamine antagonists can produce tardive dyskinesias.

The search for new CNS active compounds is focused on finding compounds with selective $5\text{-HT}_{1A}$ receptor agonist effects without detrimentally influencing central dopamine receptors.

Hellstrand et al., The Catecholamine Meeting in Jerusalem, June 1987 suggests that $5\text{-HT}_{1A}$ receptor agonists stimulate "killer cell" activity in vitro and in research animals with induced tumors.

In recent years a large body of pharmacological, biochemical and electrophysiological evidence has provided considerable support in favor of the existence of a specific population of central autoregulatory dopamine receptors located in the dopaminergic neuron itself and belonging to the D2 receptor subclass of dopamine receptors. These receptors are part of a homeostatic mechanism that modulates nerve impulse flow and transmitter synthesis and regulates the amount of dopamine released from the nerve endings.

Drugs acting on central dopamine transmission are clinically effective in treating a variety of central nervous system disorders such as parkinsonism and schizophrenia. In parkinsonism, for example, the nigro-neostriatal hypofunction can be restored by an increase in postsynaptic dopamine receptor stimulation. In schizophrenia, the condition can be normalized by achieving a decrease in postsynaptic dopamine receptor stimulation. Classical antipsychotic agents directly block the postsynaptic dopamine receptor. The same effect can be achieved by inhibition of intraneuronal presynaptic events essential for the maintenance of adequate neurotransmission, transport mechanism and transmitter synthesis.

Direct dopamine receptor agonists, like apomorphine, are able to activate the dopamine autoreceptors as well as the postsynaptic dopamine receptors. The effects of autoreceptor stimulation appear to predominate when apomorphine is administered at low doses, whereas at higher doses the attenuation of dopamine transmission is outweighed by the enhancement of postsynaptic receptor stimulation. The antipsychotic and antidyskinetic effects in man of low doses of apomorphine are likely due to the autoreceptor-stimulator properties of this dopamine receptor agonist. This body of knowledge indicates dopamine receptor stimulants with a high selectivity for central nervous dopamine autoreceptors would be valuable in treating psychiatric disorders.

INFORMATION DISCLOSURE STATEMENT

A number of 6,7,8,9-tetrahydro-N,N-dialkyl-3H-benz(e)indole derivatives are known and described, for example, L. B. Shagalow et al., Chem. Abstr. 91, 56747 v (1979) for Khim Geterotsikl. Soedin., (3), 360 (179), L. B. Shagalow et al., Chem. Abstr. 89, 146703 r (1978) for Khim. Geterotsikl. Soedin., (5), 634 (1978); Derwent Publications Ltd., Farmdoc 46000U for Netherland Pat No. 7,300,871, published Jul. 30, 1973; Derwent Publications Ltd., Farmdoc 24087B for German Offenlegunsschrift No. 2,740,836, published Mar. 22, 1979. The reported compounds lack the substituents on the 6,7,8,9-tetrahydro-1H-benz(g)indole ring system which are characteristic of the compounds in this invention.

U.S. Pat. No. 4,370,341 describes new 6,7,8,9-tetrahydro-N,N-dialkyl-3H-benz(e)indole-8-amines and U.S. Pat. No. 4,510,157 describes the isomeric 6,7,8,9-tetrahydro-N,N-dialkyl-1H-benz(g)indole-8-amines. Both of these patents claim dopamine-receptor stimulating compounds useful in the treatment of hyperprolactinemia, galactorrhea, amenorrhea, impotence, Parkinsonism, diabetes, acromegaly, hypertension and other central nervous system disorders.

The in vivo dopaminergic effects of the 6,7,8,9-tetrahydro-N,N-dialkyl-3H-benz(e)indole- 8-amines were described by Asselin et al. in J. Med. Chem. 1986, 29, 648. The resolution of 6,7,8,9-tetrahydro-N,N-dialkyl-3H-benz(e)indole-8-amines and the pharmacological testing in vivo and in vitro of the racemate, as well as, the individual enantiomers was reported very recently by Wikstrom et al. in J. Med. Chem. 1989, 32, 2273. This paper shows that it is the R-enantiomer of 6,7,8,9-tetrahydro-N,N-dimethyl-3H-benz(e)indole-8-amine which is the more active enantiomer. Surprisingly, it was shown that 6,7,8,9-tetrahydro-N,N-dimethyl-3H-benz(e)indole-8-amine, beside its dopaminergic agonist properties, also exhibits 5-HT1A agonist properties in vivo. This was further substantiated in the in vitro binding study, which showed that racemic and R-6,7,8,9-tetrahydro-N,N-dimethyl-3H-benz(e)indole-8-amine bind with high affinity to $5\text{-HT}_{1A}$ sites labelled with $^3$H-8-OH-DPAT in rat brain homogenates.

Nichols et al. recently published (J. Med. Chem. 1989, 32, 2128) the isomeric 5,6,7,8-N,N-di-n-propyl-1H-benz(f)indole-7-amine, which was shown to be dopaminergically inactive. It was speculated that the dopaminergic inactivity was due to an unfavorable direction of the indole N-H vector in the potential interaction of that compound with the central DA receptor.

SUMMARY OF THE INVENTION

This invention is to novel 6,7,8,9-tetrahydro-N,N-dialkyl-3H-benz(e)indole-8-amine compounds of Formula I

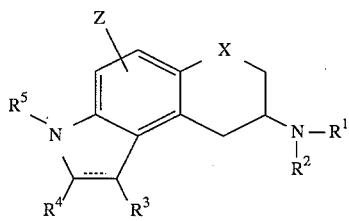

or pharmaceutically acceptable salts thereof wherein $R^1$ is H, $C_1$–$C_3$ alkyl, —$(CH_2)_n CONH_2$ wherein n is 2 to 6, $(CH_2)_n$-4,4-dimethylpiperidine- 2,6-dione-yl), or cyclopropylmethyl;

$R^2$ is hydrogen, $C_1$–$C_8$ alkyl, $C_3$–$C_8$ cycloalkyl or combined with $R^1$ to form a $C_3$–$C_8$ cycloalkyl, $C_2$–$C_8$ alkenyl, $C_2$–$C_8$ akynyl, $(CH_2)n$—X—Ar where X is O,S, or NH, 3,3,3-trifluoropropyl, —$(CH_2)_m$—$R^9$ where m is 2 or 3 and $R^9$ is phenyl, 2-thiophenyl or 3-thiophenyl;

$R^3$ is hydrogen, $C_1$–$C_3$ alkyl, 2,2,2-trifluoroethyl, 3,3,3-trifluoropropyl, formyl, CN, halogen, $CH_2OR^2$, $C(O)C(O)OR^1$, $C(O)CO$ $NR^1R^2$, —$(CH_2)_q$—$NR^1R^2$ where q is 0 to 5, C=$NOR^2$, 2(4,5-dihydro)oxazolyl, or $COR^{10}$ where $R^{10}$ is H, $R^1$, $NR^1R^2$ or $CF_3$;

$R^4$ is hydrogen, $C_1$–$C_3$ alkyl, cyclopropylmethyl, $CF_3$, 2,2,2-trifluoroethyl, CN, $CONR^1R^2$, =O, 2(4,5-dihydro)imidazolyl, 2(4,5-dihydro)oxazolyl, 2-oxazolyl, 3-oxadiazolyl, or 3,3,3-trifluoropropyl;

$R^5$ is hydrogen, $R^1$, $OCH_3$, $C(O)CH_3$ or $C(O)OR^1$;

X is
a) a valence bond,
b) $CH_2$, or
c) O, S or $NR^5$ where $R^5$ is H, $C_1$–$C_8$ alkyl, $C_3$–$C_8$ cycloalkyl, benzyl, $COR^6$ where $R^6$ is a $C_1$–$C_3$ alkyl, phenyl, or $CONR^7R^8$ where $R^7$ and $R^8$ are independently H or $C_1$–$C_3$ alkyl; and Z is a hydrogen or halogen; provided that when X is $CH_2$, at least one of $R_3$ and $R_4$ is other than hydrogen or $C_1$–$C_3$ alkyl.

Preferably, where X is $CH_2$, $R_3$ or $R_4$ is $COR^{10}$.

The compounds of this invention possess selective $5\text{-HT}_{1A}$ pharmacological properties and are useful in treating coughs (antitussive) and central nervous system disorders including depression symptoms, anxiety symptoms, panic attacks, obsessive-compulsive disturbances, senile dementia, emotional disturbances related to dementia disorders, and disturbances of sexual functions. The compounds of this invention are also useful to alleviate aggressive behavior, confusional delirious states and impotence.

In a preferred embodiment, the invention is directed to compounds of Formula I; wherein $R^1$ and $R^2$ are both $C_1$–$C_3$, $R^3$ is formyl and $R^4$, $R^5$ and Z are H. A more preferred embodiment are compounds of Formula I; wherein $R^1$ and $R^2$ are both n-propyl, $R^3$ is formyl and $R^4$, $R^5$ and Z are H.

An object of the invention is to provide compounds for therapeutic use, especially compounds having a therapeutic activity in the central nervous system. Another object is to provide compounds having an effect on the $5\text{-HT}_{1A}$ receptor in mammals including man. A further object of this invention is to provide compounds having an effect on the subclass of dopamine receptors known as the $D_2$ receptor.

DETAILED DESCRIPTION OF THE INVENTION

The Formula I compounds of this invention are identified in two ways; by the descriptive name and reference to labelled structures contained in the Formula Schemes. In appropriate situations, the proper stereochemistry is also represented in the schemes.

As used herein the term $C_n$–$C_m$ is inclusive such that a compound of $C_1$–$C_8$ would include compounds of one to 8 carbons and their isomeric forms. The various carbon moieties are defined as follows: Alkyl refers to an aliphatic hydrocarbon radical and includes branches or unbranched forms such as methyl, ethyl, n-propyl, isopropyl, n-butyl, isobutyl, sec-butyl, t-butyl, n-pentyl, isopentyl, neo-pentyl, n-hexyl, isohexyl, n-heptyl, isoheptyl, and n-octyl.

Alkenyl refers to a radical of an aliphatic unsaturated hydrocarbons having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, 2-pentenyl, 3-pentenyl, 4-pentenyl, 1-methyl-4-pentenyl, 3-methyl-1-pentenyl, 3-methyl-2-pentenyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl. Cycloalkyl refers to a radical of a saturated cyclic hydrocarbon such as cyclopropyl, cyclobutyl, cyclopentyl, cyclohexyl, cycloheptyl, or cyclooctyl.

"Ar" means aryl groups selected from phenyl, pyridyl, naphthyl or indolyl all optionally substituted with one or more of the following: $OR^1$, halogen, CN, CHO, $(CH_2)_m Ph$, $NO_2$, $SR^1$, or $NHR^1$. "Halogen" means fluorine, chlorine, bromine or iodide, preferably fluorine.

It will be apparent to those skilled in the art that compounds of this invention may contain chiral centers. The compounds of Formula I contain an asymmetric carbon atom in the aliphatic ring moiety. The therapeutic properties of the compounds may to a greater or lesser degree depend on the stereochemistry of a particular compound. The scope of this invention includes all enantiomeric or diastereomeric forms of Formula I compounds either in pure form or as mixtures of enantiomers or diastereomers.

Both organic and inorganic acids can be employed to form non-toxic pharmaceutically acceptance acid addition salts of the compounds of this invention. Illustrative acids are sulfuric, nitric, phosphoric, hydrochloric, citric, acetic, lactic, tartaric, pamoic, ethanedisulfonic, sulfamic, succinic, cyclohexylsulfamic, fumaric, maleic, and benzoic acid. These salts are readily prepared by methods known in the art.

The compounds of this invention may be obtained by one of the following methods described below and outlined in Schemes 1 and 2.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The use and administration to a patient to be treated in the clinic would be readily apparent to a person of ordinary skill in the art.

In therapeutical treatment an effective amount or a therapeutic amount of the compounds of the invention are from about 1 to about 2000 mg for oral application, preferentially 50–500 mg, and from about 0.1 to about 100 mg for parenteral application, preferentially 0.5–50 mg daily doses. The daily dose will preferably be administered in individual dosages one to 4 times daily and the dosage amounts are based on an individual having a weight of 70 kg.

The compounds of this invention where $R^1$ and $R^2$ are $C_1$–$C_3$ alkyl and $R^3$ is formyl are very selective 5-HT$_{1A}$ receptor agonists having little or no dopaminergic activity. These compounds are particularly effective anxiolytic and antidepressant agents. Other uses for these compounds include panic attach, obsessive-compulsive disturbances, and senile dementia, particularly the emotional disturbances seen in dementia disorders. In addition, central 5-HT receptor activation is believed to be involved in mediating sexual behavior. These compounds would be useful to stimulate sexual activity and to alleviate impotence.

The compounds of this invention also have been shown to have high oral potency and a long duration of action. Both these features are beneficial to effective clinical treatment.

The utility of the compounds of this invention to treat central nervous system disorders is shown in behavioral and biochemical activity in reserpine- and nonpretreated rats. Antagonism of the reserpine-induced "neuroleptic syndrome" in the rat (gross behavior)

Depletion of the monoamine stores with reserpine brings about a "neuroleptic syndrome" characterized by hypomotility, catalepsy, muscle rigidity, hunch-backed posture as well as a number of other central and peripheral signs of monoamine depletion. The whole or parts of this syndrome can be reversed by the administration of drugs that stimulate dopamine or 5-HT receptors directly or indirectly.

Stimulation of the dopamine receptors, with apomorphine for example, gives rise to both locomotion and stereotyped behavior such as sniffing, gnawing and jumping. On the other hand, stimulation of the 5-HT receptors, with 5-hydroxytryptophan (5-HTP) combined with MAO-inhibitors for example, gives rise to a very different behavior. The animals lie flat on the cage floor exhibiting forward movements with extended forepaws padding, "piano-playing," and abducted hindlegs, occasionally with some tremor in the forebody and with Straub tail, stiff tail erection.

In vivo determination of a rat brain tyrosine and tryptophan hydroxylation after reserpine pretreatment (biochemically monitored dopamine and 5-HT receptor activity).

The compounds under evaluation were tested biochemically for central dopamine and 5-HT receptor (pre- and/or post-synaptic) stimulating activity. The concept of this biochemical screening method is that a dopamine or 5-HT-receptor agonist will stimulate the receptor and through regulatory feedback systems effect a decline in tyrosine or tryptophan hydroxylating activity, respectively, and a subsequent reduction in the synthesis rate for dopamine and 5-HT in the presynaptic neuron. Dopa and 5-HTP formation, as determined after in vivo inhibition of the aromatic L-amino acid decarboxylase with NSD 1015 (3-hydroxybenzylhydrazine hydrochloride) are taken as indirect measures of dopamine and 5-HT synthesis rates, respectively as described by Wikstrom et al., J. Med. Chem., 27, 1030, 1984.

Analogous conditions probably exist also for central NA-neurons. Effects on the dopamine formation in the NA-predominated hemispheral parts (mainly cortex) may thus be considered to reflect NA-receptor-mediated changes.
Experimental procedures Rats (150–300 g) pretreated with reserpine (5 mg/kg, 18 hours before) were given the test compounds. Gross behavioral observations (changes in motility, hindleg abduction, etc.) were made. Subsequent administration of NSD 1015, decapitation, brain dissection (corpora striata, the limbic forebrain and the remaining hemispheral portions (mainly cortex) or rat brain), homogenization, centrifugation, ion-exchange chromatography and spectrofluorimetric measurements (all as described in detail by Wikstrom, et al., M. Med. Chem., 21, 864–867, 1978 and reference cited therein), or by HPLC/EC, gave the actual dopamine and 5-HTP levels. Several doses (n=4–6) were tested for each compound and brain area. The dose of a compound giving 50% of the maximal reduction of the 5-HTP level in the rat brain part was then estimated. These ED50 values are presented in Table 1.

All the compounds in Table 1 were both behaviorally and biochemically active, producing the above mentioned effects indicating either central dopamine or 5-HT receptor stimulation. The absence of significant decreases in the dopamine levels in the hemispheral brain parts suggests that none of the compounds possess central NE receptor stimulating effects at the dosage under consideration.

Table 1 shows the effects of newly synthesized compounds on DA and 5-HT synthesis rates and on motor activity in reserpine-pretreated rats. The values shown are the in vitro affinities for brain dopamine (D2), serotonin (5-HT1A) and noradrenaline (NA) (α2) receptor sites in non-pretreated rats. The animals were pretreated with reserpine (5 mg/kg, s.c.) 18 h before the experiment. Test drugs were administered and immediately thereafter the motor activity was measured in photocell motility boxes. The accumulated counts were calculated over a 30 min period (not shown). During this period the animals gross behavior were observed. "+" indicates a motoric activation of the animals. Some rats displayed typically dopaminergic mediated behavior (locomotor activity, sniffing, rearing, etc.) while others showed signs of the 5-HT behavioral syndrome (fiat body posture, abducted hind- and forelegs, and forepaw treading). "(+)" indicates that only pans of the behavioral syndromes were observed also at high doses. After the activity session the rats were injected with the decarboxylase inhibitor NSD 1015 (100 mg/kg, i.p.) and killed 30 min later. The accumulation of DOPA in the striatum and that of 5-HTP in the limbic forebrain was taken as a measure of the DA and 5-HT synthesis rates, respectively. DA receptor agonists are known to decrease the DOPA accumulation via an activation of feedback mechanisms while DA receptor antagonists are inactive in reserpine-pretreated animals. The same theory is valid for 5-HT receptor agonists and antagonists. Dose-response curves were constructed for each compound (4–5 dose levels, n=4) and the half-maximal decrease (ED50) was calculated. The maximal decrease of DOPA in striatum was found to be 80% and 50% for that of 5-HTP in the limbic region. I=inactive; no significant effect at the highest dose (shown in brackets) tested. P=partial decrease; maximal decrease was not reached at the highest dose (shown in brackets) tested. E=elevation; a statistically significant increase above the reserpine control levels was noted at the dose (shown in brackets).

rectal temperature were recorded 24 hours later in the awake rat after per oral (p.o.) or intravenous *i.v.) administration of test drugs. Recording time was at least 90 minutes. Shown are the maximal effects during the 90 min recording period expressed as the deviation from baseline values (SHR:BP; 174±6 mmHG, HR; 366±10 beats/min, RT; 38.7±0.15 C and normotensives: BP; 111±3 mmHG, HR; 369±15 beats/min, RT; 38.7±0.23 C, means ±SEM, n=7) (means ±SEM, n=3–4). In case of a biphasic response (heart rate) during the 90 rain, both maximal and minimal levels are shown period. The bioavailability calculations were based on the areas under the curves after po and iv administration.

*denotes statistical significant difference (p<0.05, or less) compared to saline treated controls (ANOVA followed by Fischer's test).

TABLE 1

| Compound | Dopa ED50 (stri) Mot. act. µmol/kg | 5-HTP ED50 (limb) µmol/kg | In vitro binding IC50 nM | | | (+/−) |
|---|---|---|---|---|---|---|
| | | | alpha2 | D2 | 5-HT1A | |
| (±)–13a | sc P (50) | 4.0 | — | 3400 | 24 | (+)5-HT |
| | po P (100) | 7.0 | | | | (+)5-HT |
| (+)–13a | sc I (12.5) | 1.0 | 140 | 11000 | 2 | +5-HT |
| (−)–13a | sc N.T. | N.T. | — | 79000 | 95 | — |
| (±)–12b | sc 0.28 | 0.1 | — | 110 | 6 | DA + 5-HT |
| (±)–13b | sc P (3.1) | 0.06 | 3700 | 710 | 1.6 | +5-HT |
| (±)–21 | sc 1.0 | I (3.1) | | 200 | 63 | +DA |
| (±)–22 | sc I (3.1) | 0.4 | — | 2100 | 8.9 | +5-HT |
| 8-OH-DPAT | sc P (35) | 0.048 | | 4300 | 8 | ++5-HT |
| | po P (61) | 3.0 | | | | ++ |

Table 2 shows the effects on blood pressure, heart rate and rectal temperature in spontaneously hypertensive rats (SHR)

TABLE 2

| comp | dose µmol/kg | ΔBP max mm Hg | ΔHR max beats/min | Δtemp max °C. | duration ΔBP min | n | Bioavail % |
|---|---|---|---|---|---|---|---|
| (±) 13a | 10.0 i.v. | −3 ± 1 | +70 ± 47* | −1.0 ± 0.15 | | 3 | |
| (±) 13a | 2.0 i.v. | −12 ± 4 | +35 ± 34 | −0.2 ± 0.40 | | 4 | |
| (±) 13a | 10.0 i.v. | −57 ± 4* | +87 ± 18 −37 ± 3 | −0.7 ± 0.33 | >90 | 3 | |
| (±) 13a | 2.0 i.v. | −60 ± 5* | +55 ± 14 −33 ± 23 | −0.2 ± 0.65 | 150 | 3 | |
| (±) 13a | 10.0 p.o. | −43 ± 22* | +24 ± 43 −39 ± 18 | +0.7 ± 0.32 | 75 | 4 | 48 |
| (±) 13a | 2.0 p.o. | −23 ± 2* | +37 ± 44 | +1.2 ± 0 | | 3 | |
| (±)-8-OH-DPAT# | 0.2 i.v. | −12 ± 6 | −83 ± 16 | −1.5 ± 0.27* | | 4 | |
| (±) 13b | 2.0 i.v. | −35 ± 3* | +110 ± 10* | −1.5 ± 0.3* | 90 | 3 | |
| (±) 13b | 10.0 p.o. | −55 ± 5* | +78 ± 11* | −1.0 ± 0.3* | >120 | 4 | 36 |
| (±) 13b | 2.0 i.v. | +14 ± 1* | −70 ± 15* | −1.6 ± 0.2* | — | 4 | |
| (±) 13b | 10.0 p.o. | +28 ± 6* | +70 ± 30* | −0.8 ± 0.4* | 60 | 3 | | and normotensive rats (#). The male spontaneously hypertensive rats (SHR), or normotensive Sprague-Dawley rats # were implanted wit catheters in the arteria carotis and vena jugularis. The blood pressure (BP), heart rate (HR) and

EXAMPLE 1

Preparation of Various Compounds of the Invention to 1-Formyl-6,7,8,9-tetrahydro-N,N-dimethyl-3H-benz(e)indole-8-amine (13a)

The following preparation is depicted in Scheme 1, below.
Method A:

A solution of o-chlorophenylacetic acid (41 g, 240 mmol) and thionylchloride (36 g, 21.7 ml, 302 mmol) in $CH_2Cl_2$ (400 ml) was refluxed for 3 hours. The solvent and unreacted tionylchloride were evaporated. The resulting oily acid chloride was redissolved in $CH_2Cl_2$ (100 ml) and poured into a cooled (sodium chloride/ice) suspension of $AlCl_3$ (130 g, 975 mmol) in $CH_2Cl_2$ (2000 ml). Ethene was passed through this mixture for 3 hours and then left overnight to slowly reach room temperature. Ice was added cautiously, shaken, separated and extracted one additional time ($CH_2C_2$). The combined organic extracts were washed (10% HCl and saturated $NaHSO_4$ in water consecutively), dried ($MgSO_4$), filtered and the solvent was evaporated to yield 55 g of a raw product, which was dissolved in EtOH. To this solution was added $Na_2S_2O_3$ (46 g, 290 mmol) dissolved in a minimal amount of water. The resulting mixture was stirred for several hours and the precipitated bisulfite adduct formed, containing some $Na_2S_2O_3$, was filtered and the residual solid was air dried (89.5 g). Prior to use in the next step, the adduct was dissolved in water, basified (5M NaOH), extracted ($Et_2O$ followed by $CH_2Cl_2$), dried ($MgSO_4$) and the solvent was evaporated to yield 29.8 g (69%) of the desired product 8-chloro-2-tetralone (1).

A mixture of compound 1 (29.8 g, 165 mmol), dipropylamine (140 ml, 102 g, 1.0 mol), p-toluenesulfonic acid (4.5 g, 29 mmol) in benzene (2500 ml) was refluxed in a Dean-Stark condenser while monitoring the progress in reaction by gas chromatography. When the reaction was completed (5 days), the solvent was evaporated to yield the crude enamine (46 g), 44 g of which was dissolved in methanol (700 ml). To the resulting stirred solution NaCNBH$_3$ (30 g, 468 mmol) was added and left overnight. The reaction mixture was evaporated and water and $CH_2Cl_2$ were added and the product was extracted with three additional portions of $CH_2Cl_2$. The combined organic extracts were dried ($MgSO_4$), filtered and the solvent was evaporated to yield 35.3 g (84%) of the product 8-chloro-2(N,N-di-n-propylamino)tetralin (2).

To neat compound 2 (14.7 g, 49.9 mmol) was added ice-cold "nitrating acid" (5.1%, 6.2 vol % $HNO_3$; 87.2%, 80.6 vol % conc $H_2SO_4$; 7.7%, 13.2 vol % water) (41 ml) dropwise at 0° C. The viscous mixture was poured onto ice and 15% NaOH (300 ml) was added. The mixture was extracted three times with $Et_2O$, the organic layer was separated, dried ($MgSO_4$), faltered and the solvent was evaporated to yield 9.6 g (62%) of the product mixture. This isomeric mixture was separated on a silica column, using flash chromatography with petroleumeter/$Et_2O$ (2:1) as eluant. The separation yielded 1.28 g (8.2%) of 2 and 1.03 g (6.7%) of 8-chloro-5-nitro- 2-(N,N-di-n-propylamino)tetralin (3a) and 1.03 g (6.7%) of 8-chloro-7-nitro-2-(N,N-di-n-propylamino)tetralin (3b). The remaining unseparated products could be recycled in a later separation.

A mixture of 3b (1.65 g), Pd/C (0.8 g) and $Et_3N$ (6 ml) in MeOH (70 ml) was hydrogenated at 36 psi in a Parr apparatus for 5 hours. The mixture was filtered through celite and the solvent was evaporated to yield 2.5 g of the raw product, which was suspended in diluted ammonia and extracted three times with $Et_2O$. The combined organic extracts were dried ($MgSO_4$), filtered and evaporated to yield 0.63 g (48%) of pure 7-amino-2-(N,N-di-n-propylamino)tetralin (4b).

To a solution of compound 1 (24.9, 0.137 mmol) in MeOH (250 ml), acetic acid (7 ml), propylamine (7.8 g, 8.5 ml, 133 mmol) and $NaBH_3CN$ (25 g, 390 mmol) were added consecutively. After standing overnight in room temperature, water, followed by 10% HCl was added. The mixture was stirred for a few hours in a well ventilated hood, allowing HCN to vaporize. The solvents were then evaporated to a residue, which was suspended in water, basified (2M NaOH) and extracted with $Et_2O$ two times and with $CH_2Cl_2$ two times. The combined organic extracts were dried ($Na_2SO_4$), filtered and the solvents were evaporated to yield 24.3 g (79%) of a crude product, which contained a small amount of starting material. Purification using flash chromatography on a silica column, eluting with $CH_2Cl_2$/MeOH (19:1) yielded 10.0 g (32%) of pure 8-chloro-2-(N-n-propylamino)tetralin (5).

To a solution of compound 5 (10.0 g, 44.7 mmol) and $Et_3N$ (6 ml) in $CH_2Cl_2$ (100 ml) was added (dropwise) propionylchloride (4.0 g, 4.0 ml, 44 mmol). This mixture was stirred at room temperature for 10 minutes, washed with aqueous (10%) $Na_2CO_3$ followed by 10% HCl. The organic phase was dried ($MgSO_4$), filtered and the solvent was evaporated to yield 12.7 g (100%) of the desired product 8-chloro-2-(N-n-propyl-N-propionylamino)tetralin (6).

To an ice-cold solution of compound 6 (12.5 g, 44.5 mmol) in nitromethane (100 ml) was added (dropwise) "nitrating acid" (32.6 ml) (see synthesis of compound 3) until all starting material was consumed (monitored with gas chromatography after basification of analytical samples and extraction with $Et_2O$). Ice-water/$Et_2O$ was added, shaken and extracted one additional time ($Et_2O$). The combined organic extracts were dried ($Na_2SO_4$), filtered and the solvent was evaporated (12.5 g, 87%). The resulting residue was chromatographed using flash chromatography on a silica column, using petroleum ether/$E_2O$ (1:2) as eluant, yielding 4.5 g (31%) of 8-chloro-5-nitro- 2-(N-n-propyl-N-propionylamino)tetralin (7a) and 3.5 g (24% of 8-chloro-7-nitro-2-(N-n-propyl-N-propionylamino)tetralin (7b). Unseparated material could be recycled in second chromatography.

Compound 7b (3.5 g, 10.8 mmol) was dissolved in EtOH (100 ml) and acidified with HCl-saturated EtOH. Pd/C (0.5 g) was added and the resulting mixture was hydrogenated in a Parr apparatus for 5 hours, filtered (Celite) and the solvent was evaporated. The residue was treated with 10% $Na_2CO_3$ and extracted into a $Et_2O$ phase, which was dried ($Na_2SO_4$), filtered and the solvent was evaporated. The product 7-amino-8-chloro-2-(N-n-propyl-N-propionylamino)tetralin (8) (2.46 g, 77%) was used without purification in the next step.

A mixture of compound 8 (2.46 g, 8.3 mmol), Pd/C (0.5 g) and $Et_3N$ (5 ml) in MeOH (100 ml) was hydrogenated in a Parr apparatus for two days. The resulting reaction mixture was filtered (Celite) and the solvent was evaporated to yield 3.0 g (138%; inc. solvent residue) of the desired product 7-amino-(N-n-propyl-N-propionylamino)tetralin (9).
Method B:

Compound 8 (3.0 g, 11.5 mmol) was suspended in dry $Et_2O$ (100 ml) and was cooled with ice prior to the addition of LiAlH$_4$ (2.6 g; 68 mmol) in portions (the progress in reaction was monitored by gas chromatography). The reaction was stirred for one additional hour. Water (2.6 ml), 15% NaOH (2.6 ml) and water (7.8 ml) were added, the solid was filtered and washed with $Et_2O$, and the resulting organic solution was washed with water, dried (Na$_2$SO$_4$), filtered and the solvent was evaporated to yield 1.83 g (64%) of the desired raw product 7-amino-2-(N,N-di-n-propylamino)tetralin (4b).

To a solution of the hydrochloride of compound 4b (1.0 g, 3.14 mmol), chloral hydrate (0.56 g, 3.4 mmol), hydroxylammoniumchloride (0.68 g, 9.8 mmol) and anhydrous Na$_2$SO$_4$ (3.45 g, 24 mmol) were added consecutively. The mixture was refluxed in a nitrogen atmosphere for 1 hour and was then allowed to reach room temperature. Ammonia (20 ml, 33% in water) was added, and the resulting liberated brown oil was extracted with 4×25 ml EtOAC. This solution was dried (Na$_2$SO$_4$), filtered and the solvent was evaporated to yield 0.85 g (90%) of the raw product 10, which was stored refrigerated prior to use in the next step.

A refrigerated solution of water (4.5 ml) in concentrated sulfuric acid (40.5 ml) was added to neat compound 10 (0.85 g, 2.82 mmol), and the mixture was stirred under nitrogen atmosphere while the temperature was slowly raised to 80° C. and maintained there for 30 minutes. The heating bath was removed and the mixture was stirred for another 1 hour before pouring it into ice (675 ml). EtOAc (50 ml) and 33% ammonia in water (125 ml) were added. The water layer was extracted with 6×50 ml EtOAc and the combined extracts were dried (Na$_2$SO$_4$), filtered and the solvent was evaporated to yield 0.78 g of 11. The crude product was purified by flash chromatography on a silica column using CH$_2$Cl$_2$: MeOH (9:1) as eluant, yielding 0.52 g (61%) of the pure product 8-(dipropylamino)-6,7,8,9-tetrahydro-3H-benz(e)indole-1,2-dione (11).

To a suspension of 0.5 g (13 mmol) LiAlH$_4$ in 125 ml of dry Et$_2$O was added 330 mg of compound (11) in 50 ml of Et$_2$O over 1 hour. The reaction was left for 2 hours at room temperature and then cooled to 0° C. In order to destroy excess LiAlH$_4$ 10 ml EtOAC was added. After 0.5 h 0.5 ml water, 0.5 ml 15% NaOH and 1.5 ml water was added consecutively and then allowed to reach room temperature. The mixture was dried with Na$_2$SO$_4$, filtered and the solvent was evaporated to yield 270 mg (57%) of the crude product 6,7,8,9-tetrahydro-N,N-dipropyl-3H-benz(e)indole-8-amine (12b).

6,7,8,9-Tetrahydro-N,N-dimethyl-3H-benz(e)indole-8-amine(12a)compound was synthesized from 8-chloro-2-tetralone (1) by the same route as outlined above for the synthesis of compound 12b.

To dimethylformamide (30 ml) was added (dropwise via syringe at −10° to −20° C.) POCl$_3$ (0.5 ml, 0.84 g, 5.5 mmol). A solution of 6,7,8,9-tetrahydro-N,N-dimethyl-3H-benz(e)indole-8-amine (12a) (500 mg, 2.3 mmol) in DMF (15 ml) was thereafter added dropwise to the cold POCl$_3$/DMF solution, and the resulting solution was heated to 55° C. in 1.5 hours. The reaction mixture was, after cooling to room temperature, poured into ice, basified (2M NaOH) and saturated with NaCl. Extraction three times with CH$_2$Cl$_2$, drying (MgSO$_4$) and evaporation of the solvent yielded 300 mg (54%) of a solid material 1-formyl-6,7,8,9-tetrahydro-N,N-dimethyl-3H-benz(g)indole-8-amine (13a). GC/MS (HP-5970A) showed: M$^+$ at m/e=242 (16%) and the base peak at m/e=170. Other prominent peaks at m/e=115 (28%), 143 (68%) and 199 (56%).

EXAMPLE 2

Preparation of
(+)-and(−)-1-formyl-6,7,8,9-tetrahydro-N,N-dimethyl-3H-benz(e) indole-8-amine (13a)

The enantiomers of 13a were prepared in the same way as the racemate from the corresponding enantiomers of 13a (see Wikstrom et al., J. Med. Chem. 1989, 32, 2273). In these cases the purification was completed via flash chromatography using MeOH as eluant.

(+)-13a:[α]$^{20}$D=+97.3° (c 1.0, MeOH) MS (HP-5970A), m/e=242 (37) M$^+$, 170 (100), 143 (61), 199 (48), 198 (28).
(−)-13a:[α]$^{20}$D=−95.2° (c 1.0, MeOH) MS (HP-5970A), m/e=242 (33) M$^+$, 170 (100), 143 (56), 199 (48), 198 (28).

EXAMPLE 3

Preparation of
1-formyl-6,7,8,9-tetrahydro-N,N-dipropyl-3H-benz(e)indole-8-amine (13b)

Using the same procedure as described for the preparation of compound 13a, 13b (11 mg) was synthesized from 12b (20 mg).

GC/MS (HP-5970A) showed: M$^+$ at m/e=298 (12%) and the base peak at m/e =198. Other prominent peaks at m/e=154 (19%), 170 (56%) and 269 (82%).

EXAMPLE 4

Preparation of
8-(N-propionyl-N-n-propylamino)-8,9-dihydro-2H-pyrano-(3,2-e)-indol (21)

The following preparation is depicted in Scheme 2, below.

A solution of 3-nitro-2H-chromene (2 g, 11.2 mmol), synthesized by known methods (Dauzonne, D.; Royer, R. Synthesis 4, 348, 1984) in dry THF (50 ml) was reduced with LiAlH$_4$ (2 g, 52.7 mmol). The mixture was stirred for 10 min at room temperature. Excess hydride was quenched by addition of water (2 ml), 15% NaOH (2 ml) and water (6 ml). The mixture was filtered and the solvent evaporated yielding the product as an oil. The amine was extracted with 5% HCl/EtOAC. The phases were separated and the water layer was treated with activated carbon and filtered. After adjusting the pH to 11 with 1N NaOH, the water phase was extracted with EtOAC. The organic layer was dried (Na$_2$SO$_4$) and the solvent was evaporated, yielding 1.2 g (72%) of 3-aminochroman 14 as an oil.

Propionyl chloride (1.1 g, 11.5 mmol) was added to a mixture of 14 (1.2 g, 8.0 mmol) in CH$_2$Cl$_2$ and 10% aqueous Na$_2$CO$_3$ and stirred for 2 hours. Additional propionyl chloride (1.1 g, 11.5 mmol) was added and the mixture stirred overnight. The phases were separated and the organic layer was dried (MgSO$_4$). The solvent was evaporated and the crude amid was treated with LiAlH4 (1 g, 26.4 mmol) in dry THF for 8 hours at room temperature. Since the reduction was not completed, additional LiAlH$_4$ (0.5 g, 13.2 mmol) was added and the mixture refluxed for 1 hour. Excess of hydride was quenched by addition water (1.5 ml), 15% NaOH (1.5 ml) and water (4.5 ml). The mixture was filtered and the solvent evaporated yielding 1.1 g (72%) of 3-(N-n-propylamino)chroman (15) as an oil. The amine was converted to its hydrochloride with HCl-saturated EtOH and recrystallized from EtOH-ether. m.p. 203° C.

Propionyl chloride (2.8 g, 29 mmol) was added to a mixture of 15 (1.2 g, 6.4 mmol) in CH$_2$Cl$_2$ and 5% aqueous NaOH. The mixture was stirred for 30 rain and separated. The organic layer was extracted with water, separated and dried (MgSO$_4$). The crude product was chromatographed (SiO$_2$) with light petroleum-ether (2:1) as eluant yielding 0.98 g (62%) of 3-(N-propionyl-N-n-propylamino)chroman (16).

To an ice cool solution of 730 mg (2.96 mmol) 3-(N-propionyl-N-n-propylamino)chroman (16) in nitromethane (15 ml) was a mixture of fuming nitric acid (0.70 ml) and concentrated sulphuric acid (1.42 ml) added. The solution was stirred for 90 rain at 0° C. The reaction mixture was poured out on ice and the product was extracted with dichloromethane. The organic layer was washed with water and 5% aqueous $Na_2CO_3$. The organic layer was separated, dried ($MgSO_4$) and the solvent was evaporated yielding 700 mg (81%) of 6-nitro-3-(N-propionyl-N-n-propylamino)chroman (17).

A solution of 6-nitro-3-(N-propionyl-N-n-propylamino)chroman (17) (700 mg, 2.40 mmol) in glacial acetic acid (50 ml) was treated with zinc dust (1.0 g). The mixture was stirred at 50° C. for 90 minutes. The solution was filtered and acetic acid evaporated at reduced pressure. The product was dissolved in $CH_2Cl_2$ and washed with 5%-aqueous $Na_2CO_3$. The organic layer was separated, dried ($Na_2SO_4$) and the solvent was evaporated. The crude product was chromatographed on silica (60 g), with $CH_2Cl_2$-$CH_3OH$ (19:1) as eluant, yielding 350 mg (56%) of 6-amino-3-(N-propionyl-N-n-propylamino)chroman (18) as an oil.

To a solution of 6-amino-3-(N-propionyl-N-n-propylamino)chroman (18), hydrochloride (369 mg, 1.24 mmol) in deionized water (5 ml) was chloral hydrate (221 mg, 1.33 mmol), hydroxylamine hydrochloride (269 mg, 3.86 mmol) and anhydrous sodium sulphate (1.36 g) added. When the mixture was refluxed for one hour under nitrogen an oil started to precipitate. The reaction mixture was cooled to room temperature and made alkaline with diluted ammonium hydroxide (7 ml, 3.3%-$NH_3$). The mixture was extracted with $CH_2Cl_2$. The organic layer was dried and the solvent was evaporated yielding 358 mg (91%) of 6-(2-hydroxyimino)-3-(N-propionyl-N-n-propylamino)chroman (19) as crude product, that was used as such in the next step.

To an ice cool of solution of concentrated sulfuric acid (15.2 ml) and water (1.7 ml) was added 6-(2-hydroxyimino)-3-(N-propionyl-N-n-propylamino)chroman (19) (358 mg, 1.12 mmol). The mixture was stirred at room temperature for 30 minutes under argon atmosphere. The temperature was then raised to 80° C. and maintained for 30 minutes. The solution was allowed to cool to room temperature and stirred at this temperature for 1 hour. The reaction mixture was poured onto crushed ice (260 ml). Dichloromethane was added and the mixture was made alkaline with ammonium hydroxide (47 ml, 33%). The phases were separated and the organic layer was extracted with water, separated, dried ($MgSO_4$) and the solvent was evaporated yielding 240 mg of an oil. The crude product was chromatographed on silica (40 g), with $CH_2Cl_2$-$CH_3OH$ (30:1) as eluant yielding 100 mg (28%) of 8-(N-propionyl-N-n-propylamino)-8,9-dihydro-2H-pyrano-(3,2-e)-indol-1,2-dione (20).

To a suspension of $LiAlH_4$ (280 rag, 7.37 mmol) in dry THF (30 ml) was added 8-(N-propionyl-N-n-propylamino)-8,9-dihydro-2H-pyrano-(3,2-e)-indol-1,2-dione (20) (70 mg, 0.22 mmol) dissolved in dry THF (20 ml) added dropwise during 90 minutes. The mixture was stirred for additional 90 minutes. Excess of hydride was quenched by addition of EtOAc (0.5 ml), followed by water (0.3 ml), 15% NaOH (0.3 ml) and water (0.9 ml). The mixture was filtered and the solvent evaporated yielding 83 mg of an oil. The crude product was chromatographed on silica with light petroleum/$Et_2O$ (2:1) as eluant yielding 20 mg (33%) of 8-N,N-dipropylamino-8,9-dihydro-2H-pyrano-(3,2-e)-indol (21).

GC/MS (HP-5970A): m/e=272 (33) M$^+$ 98 (100), 70 (65), 172 (64), 127 (38). $^1$H NMR (CDCl$_3$)δ0.80–1.0 (t, 6H), 1.4–1.6 (m, 4H), 2.45–2.65 (q, 4H), 2.9–3.1 (m, 1H), 3.25–3.4 (m, 1H), 3.8–3.9 (t, 1H), 4.3–4.4 (m, 1H), 6.4–6.5 (s, br, 1H), 6.7–6.8 (d, 1H), 7.1–7.2 (d, 1H), 7.15–7.25 (s, br, 1H), 8.1–8.2 (s, br, 1H).

EXAMPLE 5

Preparation of 1-formyl-8-N,N-dipropylamino-8,9-dihydro-2H-pyrano-(3,2-e)indole (22)

To dry dimethylformamide (10 ml) at 0° C. was added POCl$_3$ (0.080 ml, 0.88 mmol). The solution was stirred in an ice bath for 10 minutes. Thereafter, compound 21 (40 mg, 0.15 mmol) was dissolved in dry dimethylformamide (4 ml). The solution was stirred for 10 minutes at 0° C. and for an additional 30 minutes at room temperature. The reaction mixture was placed in an oil bath and stirred at 50° C. for 2 hours under nitrogen. Another portion of POCl$_3$ (0.040 ml, 0.44 mmol) was added and the reaction mixture was stirred for another 2 hours at 50° C.

The mixture was allowed to reach room temperature and was then poured onto crushed ice (50 ml) and extracted with $CH_2Cl_2$ (30 ml), after adjusting the pH to 11 with $Na_2CO_3$ (10%). The phases were separated and the organic layer was extracted with water, separated, dried ($Na_2SO_4$), filtered and the solvent was evaporated, yielding 30 mg of an oil. The crude product (22) was chromatographed (SiO$_2$) with $CH_2Cl_2$/MeOH (30:1) as eluant, yielding 25 mg.

GC/MS (HP-5970A), m/e=300 (26) M$^+$, 200 (100), 271 (73), 98 (57), 201 (41).

$^1$H NMR (CDCl$_3$)δ0.80–1.0 (t, 6H), 1.4-1.6 (m, 4H), 2.5–2.7 (q, 4H), 3.2–3.25 (m, 1H), 3.425–3.6 (m, 1H), 3.8–3.95 (t, 1H), 4.3–4.4 (m, 1H), 6.8–6.9 (d, 1H), 7.1–7.2 (d, 1H), 7.9 (s, 1H), 9.0 (s, br, 1H), 10.1 (s, 1H).

EXAMPLE 6

6-Amino-3-(di-n-propylamino)chroman (23)

To a solution of 6-amino-3-(N-propionyl-N-n-propylamino)chroman(18) (300 mg, 1.03 mmol) in anhydrous diethyl ether was added LiAlH$_4$ (300 mg, 7.89 mmol). The mixture was stirred for 1.5 hours at room temperature. Excess hydride was quenched by addition water (0.5 ml), 15% sodium hydroxide (0.3 ml) and water (0.9 ml). The mixture was filtered and the solvent evaporated yielding 216 mg (85%) of 23 as an oil.

GC/MS (HP-5970A), m/e=248 (34) M$^+$, 114 (100), 148 (54), 98 (47), 219. (35).

$^1$H NMR (CDCl$_3$)δ0.8–1.0 (t, 6H), 1.4–1.65 (m, 4H), 2.45–2.6 (t, 4H), 2.7–2.8 (m, 2H), 3.1–3.25 (m, 1H), 3.7–3.8 (t, 1H), 4.2–4.3 (m, 1H), 6.4–6.5 (m, 2H), 6.6–6.7

EXAMPLE 7

6-(2-Hydroxyimino)-3-(di-n-propylamino)chroman (24)

To a solution of 23, dihydrochloride (211 mg, 0.66 mmol) in deionized water (3 ml) was added chloral hydrate (132 mg, 0.79 mmol), hydroxylamine hydrochloride (161 mg, 2.31 mmol) and anhydrous sodium sulphate (0.81 g). The mixture was refluxed for one hour under nitrogen. The reaction mixture was cooled to room temperature and made alkaline with diluted ammonium hydroxide (10 ml, 3.3% $NH_3$). The mixture was extracted with $CH_2Cl_2$. The organic layer was dried and evaporated yielding 186 mg (92%) of 24 as a crude product, which was used without further purification in the next step.

EXAMPLE 8

8-(Di-n-propylamino)-8,9-dihydro-2H-pyrano(3,2-e)indole-1,2-dione(25)

To an ice cooled solution of concentrated sulphuric acid (8.3 ml) and water (0.93 ml) was added 24 (186 mg, 0.61 mmol). The mixture was stirred at room temperature for 30 minutes under argon atmosphere. The temperature was then raised to 80° C. and maintained there for 30 minutes. The solution was allowed to cool to room temperature and stirred at this temperature for 1 hour. The reaction mixture was poured onto crushed ice (140 ml). Dichloromethane was added and the mixture was made alkaline with ammonium hydroxide (25 ml, 33%). The phases were separated and the organic layer was extracted with water, separated, dried ($MgSO_4$) and the solvent was evaporated yielding 240 mg of an oil. The crude product was chromatographed on silica (40 g), with $CH_2Cl_2$/MeOH (30:1) as eluant, yielding 90 mg (49%) of 25.

$^1$H NMR ($CDCl_3$)δ0.85–1.0 (t, 6H), 1.4–1.55 (m, 4H), 2.4–2.6 (m, 4H), 2.85–3.0 (q, 1H), 3.1–3.25 (q, 1H), 3.3–3.4 (d, d, 1H), 3.8–3.9 (t, 1H), 4.2–4.3 (d, 1 H), 6.6–6.7 (d, 1H), 6.9–7.0 (d, 1H), 7.7 (s, br, 1H).

EXAMPLE 9

Preparation of 1-(2,2,2-trifluoromethyl-1-oxoethyl)-6,7,8,9-tetrahydro-N,N-di-n-propyl-8-amino-3H-benz(e)indole To a solution of 200 mg (0.74 mmol) of 6,7,8,9-tetrahydro-N,N-di-n-propyl-8-amino-3H-benz(e)indole in 4 ml DMF was added 40 mg (0.86 mmol) sodium hydride (55% mineral oil dispersion) at 0° C. After a few minutes 100 mg (0.80 mmol) benzylchloride was added. The reaction progress was monitored by GLC. After stirring for two hours at 0° C., another 10 mg (0.022 mmol) sodium hydride dispersion and 25 mg (0.20 mmol) benzylchloride were added consecutively and the reaction was completed within another 30 minutes. The reaction mixture was poured into water and extracted with ether. The water phase was extracted with another portion of ether. The combined ether extracts were dried ($MgSO_4$), filtered and evaporated under reduced pressure. Ethanol (99%) was added and the solvents were evaporated again. This procedure was repeated to get rid of excess DMF and yielded 284 mg (107%) of 3-benzyl-6,7,8,9-tetrahydro-N,N-di-n-propyl-8-amino-3H-benz(e)indole (X).

To a solution of X (270 mg, 0.75 mmol) in triethylamine (0.5 ml) and dichloromethane (0.5 ml) was added trifluoroacetic anhydride (307 μl, 206 mg, 0.98 mmol) and the mixture was stirred at room temperature overnight. Water was added and the mixture was stirred for several hours in room temperature. The organic layer was evaporated and the raw product (583 mg) 3-benzyl-1-(1,1,1-trifluoroacetyl)-6,7,8,9-tetrahydro-N,N-di-n-propyl-8-amino-3H-benz(e)indole (XI) was chromatographed on a $SiO_2$-column, using acetone as eluant. Yield 350 mg (102%).

A mixture of 0.338 mg (0.74 mmol) of XI and 230 mg (6.0 mmol) $LiAlH_4$ in THF (20 ml) (refluxed and distilled from potassium) was refluxed for three days and then boiled to dryness and refilled with THF. The remaining $LiAlH_4$ was destroyed by the cautious addition of 0.3 ml water, 0.3 ml 15% NaOH and 0.9 ml. The resulting precipitate was filtered off and the ethereal solution was evaporated to yield 190 mg (73%) of a raw product 1-(1,1,1-trifluoroethyl)-6,7,8,9-tetrahydro-N,N-di-n-propyl-8-amino-3H-benz(e)indole (XII) which was chromatographed on a $SiO_2$ column using methanol as eluant. The pure fractions were collected yielding 44 mg of an oil, which was convened to the hydrochloride with HCl-saturated ether.

MS (HP-5970A), m/e=352 (17) $M^+$, 252 (100), 329 (34), 225 (17), 167 (16).

EXAMPLE 10

Preparation of 1-dimethylaminomethyl-6,7,8,9-tetrahydro-N,N-dipropyl-8-amino-3H-benz(e)indole.

A stock solution of Mannich reagent was prepared by mixing together at 0° C. glacial acetic acid (40 mL), 1,4-dioxane (40 mL), 37% aqueous formaldehyde (3.2 mL), and 40% aqueous dimethylamine (4.8 mL). A portion of this solution (2.5 mL) was transferred to a 4 mL reaction vessel, cooled to 0 C., and treated dropwise with a solution of 12b, Scheme 1, (215 mg) in 1,4-dioxane (1 mL). The reaction was stirred at 0° C. for 2 hrs, then warmed to room temperature and stirred for an additional 16 hours. The reaction mixture was then added to water (20 mL) and the resulting solution was made basic by the addition of 2N NaOH. The aqueous suspension was extracted with dichloromethane (3×15 mL) and the combined organic phases were dried over anhydrous $MgSO_4$, filtered, and concentrated to a tan solid. Trituration with hexane afforded the pure product (109 mg) as a white, free-flowing powder. (Formula I where $R^1$ and $R^2$ are propyl, $R^3$ is dimethylaminomethyl, $R^4$ is hydrogen, $R^5$ is hydrogen, Z is hydrogen.)

1H NMR (CDCl3) d 0.91 (t, 6H), 1.52 (m, 4H), 1.69 (m, 1H), 2.05 (m, 1H), 2.25 (s, 6H), 2.56 (m, 4H), 2.94 (m, 2H), 3.06 (m, 2H), 3.37–3.74 (q, 2H), 3.80 (m, 1H), 6.89 (d, 1H), 7.00 (d, 1H), 7.10 (d, 1H), 7.93 (br s, 1H). For the bis-HCL salt: MS m/e=399 (M+), 182 (100), 226 (96), 183 (79), 253 (72), 184 (64), 58 (50).

EXAMPLE 11

1-(N,N-diethylglyoxyamide)-6,7,8,9-tetrahydro-N,N-dipropyl-8-amino-3H-benz(e)indole A solution of 12b, from Scheme 1, (213 mg) in diethyl ether (4 mL) was cooled to 0° C. under nitrogen and treated dropwise with oxalyl chloride (0.20 mL). The resulting yellow suspension was stirred at 0° C. for 30 minutes, then warmed to room temperature and stirred for an additional 30 minutes. The reaction was re-cooled to 0° C. and treated dropwise with a solution of diethylamine (0.8 mL) in ether (1 mL). After stirring for 2 hours at room temperature, the reaction mixture was partitioned between saturated aqueous $NaHCO_3$ and t-butylmethyl ether (TBME) and the aqueous phase was extracted twice more with TBME. The combined organic layers were washed once with water and once with brine, dried over $MgSO_4$, filtered, and concentrated to a thick oil. This material was purified by chromatography on silica gel using dichloromethane containing 5% 3M $NH_3$ in methanol as the eluent. In this manner the subject compound (242 mg) was obtained as a yellow foam. (Formula I where $R^1$ and $R^2$ are propyl, $R^3$ is diethylglyoxyamide, $R^4$ is hydrogen, $R^5$ is hydrogen, Z is hydrogen.)

1H NMR (CDCl3) d 0.91 (t, 6H), 1.14 (t, 3H), 1.23 (t,

3H), 1.57 (m, 4H), 1.71 (m, 1H), 2.08 (m, 1H), 2.67 (t, 4H), 2.94 (m, 2H), 3.05 (m, 1H), 3.16–3.34 (m, 3H), 3.49 (q, 2H), 3.80 (d of d, 1H), 6.94 (d, 1H), 7.12 (d, 1H), 7.71 (s, 1H), 9.80 (br s, 1H). MS m/e=397 (M+), 368 (100), 196 (73), 100 (38), 369 (25).

EXAMPLE 12

1-Bromo-6,7,8,9-tetrahydro-N,N-dimethyl-8-amino-3H-benz[e]indole

A solution of 50 mg (0.23 mmol) 6,7,8,9-tetrahydro-N,N-dimethyl-8-amino-3H-benz[e]indole in 10 ml triethylamine was treated portion-wise with 200 mg (0.62 mmol) pyridinium hydrobromide perbromide. The progress in reaction was monitored by GLC and was complete within a few hours. Solid material was filtered and the resulting solution evaporated to a residue which was redissolved in dichloromethane, filtered and evaporated again to yield 45 mg (67%) of the desired product (unstable).: MS m/e 292 (M+, 58), 292 (M+ +2 (isotope), 52), 221 (100), 223 (94), 115 (71), 168 (48), 167 (38), 170 (24), 247 (35), 249 (32).

EXAMPLE 13

1-Chloro-6,7,8,9-tetrahydro-N,N-dipropyl-8-amino-3H-benz[e]indole

A solution of 43 mg (0.32 mmol) N-Chlorosuccinimide and 70 mg (0.26 mmol) 6,7,8,9-tetrahydro-N,N-dipropyl-8-amino-benz[e]indole in 4 ml tetrahydrofuran was stirred at room temperature for 2 hours. The solution was washed (saturated sodium carbonate solution), dried (magnesium sulfate), filtered and evaporated to yield 84 mg of a crude product which was eluated on a silica column using methanol as eluant to give 28 mg (29%) of the desired material.: MS m/e 306 (7, M+), 304 (20, M+−2(isotope-e)), 204 (100), 275 (77), 169 (44), 177 (20).

EXAMPLE 14

1-Cyano-6,7,8,9-tetrahydro-N,N-dipropyl-8-amino-3H-benz[e]indole

To an ice-cooled solution of 500 mg (1.85 mmol) 6,7,8,9-tetrahydro-N,N-dipropyl-8-amino-3H-benz[e]indole in 10 ml of acetonitrile in an inert atmosphere was added dropwise a solution of 360 mg (2.50 mmol) chlorosulphonyl isocyanate in 1.5 ml acetonitrile. After stirring for 20 minutes a solution of 154 mg dimethylformamide in 10 ml acetonitrile was dropwise added and the resulting mixture was stirred for 1 hour. The mixture was poured in ice and basified using dilute ammonia. After extraction 6 times with dichloromethane the organic solution was dried (MgSO$_4$), filtered and evaporated. Methanol was added until most of the material was dissolved. Undissolved material was filtered (40 mg of product 90% purity) and the solution was reduced to one half. The precipitated product was filtered off (180 mg pure product). From the mother liquor additional material (220 mg) was recovered giving a total crude yield of 80%.: 1H NMR (300 MHz, DMSO-d6) d 0.9 (t, 6H), 1.45 (q, 4H), 1.6 (m, 1H), 1.95 (br. d, 1H), 2.45 (m, 4H), 2.9 (m, 4H), 3.4 (solvent-hidden, "1"H)*, 6.95 (d, 1H), 7.25 (d, 1H), 8.15 (s, 1H), 12.0(br. s, 1H); 13C NMR (300 MHz, DMSO-d6)d 11.78 (CH3), 21.71 (CH2), 28.64 (CH2), 29.38 (CH2), 52.02 (CH2), 56.18 (CH), 83.13 (C), 110.43 (CH), 118.20 (C), 124.66 (CH), 125.07 (C), 127.61 (C), 128.86 (C), 133.43 (C), 134.50 (CH); MS m/e 295 (M+, 6), 195 (100), 266 (50), 193 (20), 179 (15), 196 (15).

EXAMPLE 15

3-(N-Propionyl)aminoquinoline

Propionic acid chloride (17 g, 184 mmol) was added at ambient temperature to a solution of 25 g (174 mmol) 3-aminoquinoline and 26 ml triethyl amine in 400 ml dichloromethane. After stirring for 2 hours in 200 ml 10% sodium carbonate was added and the mixture was shaken and separated. The aqueous phase was extracted 3 times with dichloromethane and 3 times with ethyl acetate. The combined organic phases where dried (magnesium sulfate), filtered and evaporated to yield 35.0 g (100%) of the desired product.

EXAMPLE 16

3-(N-Propionyl)amino-1,2,3,4-tetrahydroquinoline

To a solution of 17.4 g (86.9) 3-(N-propionyl)aminoquinoline and 20.0 g (317 mmol) ammonium formate in 150 ml methanol was added 1.0 g Pd/C cautiously under an inert atmosphere. After stirring at ambient temperature for 2 days the reaction stopped. The ratio between starting material and product was approximately 1:1 (monitored by GLC). The mixture was filtered on Celite and evaporated to a residue from which the product was extracted into diethyl ether. The ether solution was dried (magnesium sulfate), filtered and evaporated. The product/starting material mixture was then recharged in a similar manner using the same amounts of reactants. After additional 4 days the reaction was completed and worked-up as above to yield 9.7 g (55%) of reasonably pure material.: MS m/e 204 (M+, 4), 130 (100), 131 (45), 118 (8), 91 ( 5).

EXAMPLE 17

3-(N-Propyl)amino-1,2,3,4-tetrahydroquinoline

To a ice-cooled solution of 3.2 g (15.6 mmol) 3-(N-propionyl)amino-1,2,3,4-tetrahydroquinoline in 50 ml dry diethyl ether and 80 ml dry tetrahydrofurane was 3.0 g (79 mmol) lithium aluminum hydride added. The mixture was gently heated to reflux and kept that way for 5 days. Ethyl acetate (4.5 ml), 3.0 ml water,3.0 ml 15% sodium hydroxide and 9 ml water was added consecutively. The precipitate appearing after 5 minutes was filtered off and washed with diethyl ether. Evaporation of the etheric solution yielded 2.66 g (89%) of the desired product.: 13C NMR () d 11 (76), 23.46, 33.71, 46.41, 48.98, 50.43, 113.79, 117.29, 119.37, 126.87, 130.06, 144.09; MS m/e 190 (M+, 17), 132 (100), 130 (32), 72 (22), 118 (17), 131 (17).

Example 18

1-N-Propionyl-3-(N'-propyl-N'-propionyl)amino-1,2,3,4-tetra-hydroquinoline

To a solution of 2.5 g (13.1 mmol) 3-(N-propyl)amino-1,2,3,4-tetrahydroquinoline and 10 ml triethylamine in 100 ml dichloromethane was added 2.5 g (27.0 mmol) drop-wise at room temperature. After stirring for 15 minutes the reaction was completed and the reaction mixture was washed with 10% sodium carbonate and 10% hydrochloric acid, dried (magnesium sulfate), filtered and evaporated to yield 4.0 g product (100%).

EXAMPLE 19

1-N-Propionyl-3-(N'-propyl-N'-propionyl)amino-6-nitro-1,2,3,4-tetrahydroquinoline To a cooled (NaCl-ice, −5° C.) solution of 3.3 g (10.9 mmol) of 1-N-Propionyl- 3-(N'-propyl-N'-propionyl)amino-1,2,3,4-tetrahydroquinolinein 80 ml acetic acid anhydride was added copper (II) nitrate ($2H_{20}$) and the temperature was allowed to slowly reach ambient temperature. The reaction was monitored on GLC and found to be complete after 5 hours. After filtering and washing through Celite the solution was washed with 10% sodium carbonate, dried (magnesium sulfate), charcoal, filtered (Celite) and evaporated yielding a raw product as an oil (5.5 g). The isomeric mixture was separated on silica column using flash chromatography technique. The elution started with diisopropyl ether/isopropanol (9:1) and gave 0.7 g unidentified material and proceeded with diethyl ether to give 1.1 of 1-N-propionyl-3-(N'-propyl-N'-propionyl)amino-6-nitro-1,2,3,4-tetrahydro-quinoline, 0.3 g isomeric mixture and 0.3 g of an isomer. Tot.:1.7 g, 45%).: 1H NMR (300 MHz, CDCl3) d 0.95 (t, 3H), 1.0–1.3 (two t, 6H) 1.65 (sext, 2H), 2.35 (q, 2H), 2.55 (m, 2H), 3.0–3.1 (two d, 1H), 3.20 (m, 2H), 3.25–3.40 (two d, 1H), 3.85 (t, 1H), 4.10 (br. d, 2H), 7.65 (d, 1H), 8.05 (s and d?, 2H); 13C NMR (300 MHz, CDCl3) d 9.35 (9.35, CH3), 9.51 (CH3), 11.19 (CH3), 23.92 (CH2), 27.16 (CH2), 28.07 (CH2), 31.19 (CH2), 45.59 (CH2), 53.08 (CH), 121.67 (CH), 124.47 (CH), 124 (94, CH), 130.95 (C), 144.10 (C), 144.16 (C), 173.33 (C), 174.21 (C),.; MS m/e 232 (M+-two propionyl, 16), 176 (100), 175 (42), 57 (40), 116 (21), 159 (20).

EXAMPLE 20

1-N-Propionyl-3-(N'-propyl-N'-propionyl)amino-6-amino-1,2,3,4-tetrahydroquinoline A mixture of 1.0 g (2.9 mmol) 1-N-Propionyl-3-(N'-propyl-N'-propionyl)amino-6-nitro-1,2,3,4-tetrahydroquinoline, 1.6 g ammonium formate and 0.17 g Pd/C in 100 ml ethanol was stirred in room temperature for 2 days, following the progress in reaction with GLC. The mixture was filtered on Celite and evaporated to a material which was suspended in diethyl ether. The suspension was filtered and evaporated to yield 0.90 g (98%) of the desired material.: 1H NMR (300 MHz, CDCl3) d 0.90 (p or two t, 3H), 1.15 (m, 6H), 1.65 (br sext, 2H), 2.35 (q, 2H), 2.45 (q, 2H), 3.8 (br. s, 2H), 3.15 (m, 2H), 4.75 (br s, 2H), 4.90 (m, 2H), 4.0–4.5 (two m, 1H), 6.5 (m, 2H), 6.9 (br. s, 1H); MS m/e 317 (M+, 6), 145 (100), 146 (83), 202 (53), 147 (16), 57 ( 10).

EXAMPLE 21

1-N-Propyl-3-(N',N'-dipropyl)amino-6-amino-1,2,3,4-tetrahydroquinoline

To a solution of 0.85 g (2.68 mmol) 1-N-propionyl-3-(N'-propyl-N'-propionyl)amino-6-amino-1,2,3,4-tetrahydroquinoline in dry diethyl ether was 0.50 g lithium aluminum hydride added in portions at room temperature. The mixture was stirred for one hour. Water (0.5 ml), 0.5 ml 10% sodium hydroxide and 1.5 ml water was then added consecutively. After stirring for 10 minutes the precipitate was filtered off and the etheric solution evaporated to yield 0.74 g (96%) of the desired product.: 1H NMR ( ) d 0.90 (p or two t, 9H), 1.45 (sext, 4H), 1.55 (sext, 2H), 2.45 (t, 4H), 2.70 (m, 2H), 2.90–3.30 (m, 6H), 6.40–6.50 (m, 3H); 13C NMR ( ) d 11 (62, CH3), 11.82 (CH 3), 19.17 (CH2), 22.03 (CH2), 31.00 (CH2), 51.70 (CH2), 52.71 (CH2), 53.89 (CH 2), 54.48 (CH), 112.26 (CH), 114.72 (CH), 117.64 (CH), 123.96 (CH), 136.32 (CH), 138.90 (CH); MS m/e 289 (M+, 28), 114 (100), 189 (44), 161 (34), 147 (33), 187 (30).

EXAMPLE 22

1-Formyl-3-(N',N'-dipropyl)amino-6-amino-1,2,3,4-tetrahydroquinoline

A mixture of 112 mg (0.28 mmol) 1-N-propyl-3-(N',N'-dipropyl)amino-6-amino-1,2,3,4-tetrahydroquinoline,50 mg (0.34 mmol) chloral hydrate 60 mg (0.89 mmol) hydroxylamine hydrochloride and 240 mg sodium sulfate in 0.9 ml water was heated at reflux temperature for 1.5 hours. After cooling and basification (10% ammonia) the mixture was extracted 3 times (ethyl acetate), dried (magnesium sulfate), filtered and evaporated to a residue of 109 mg which was dissolved in cold (approx. −20° C.) 10% water in sulfuric acid. Heating (80° C.) the mixture for 1 hour and work-up as above yielded 60 mg material, which was dissolved in diethyl ether and treated with 50 mg lithium aluminum hydride at room temperature. After stirring for 4 hours in 50 μl water, 50 μl 10% sodium hydroxide and 150 μl water was added consecutively. Filtering and evaporation gave 47 mg, which was chromatographed on a silica column using diethyl ether followed by methanol as eluant. Only 4 mg of the desired material could be recovered from the rather complex product mixture.: MS m/e 313 (M+, 30), 114 (100), 213 (52), 171 (34), 211 (31), 183 (30).

To make the formyl compound, 4 mg indole compound in 0.5 ml dimethyl formamide was treated with 10 μl phosphorous oxychloride in 1 ml dimethyl formamide at −5° C. After 1 hour the mixture was poured on ice, made basic (5M sodium hydroxide) and extracted with ethyl acetate. Evaporation yielded a crude material (20 mg) which contained approx 10% of the desired product (GC-MS). Purification on a silica column was not successful.: MS m/e 341 (M+, 33), 241 (100), 114 (100), 199 (56), 169 (46), 211 (44).

EXAMPLE 23

6-Fluoro-1,2,3,4-tetrahydro-2-naphthalene

A solution of 100 g (0.65 mol) 4-fluorophenyl acetic acid and 164 g (1.37 mol) thionyl chloride in 200 ml dichloromethane was refluxed for 4 hours. The mixture was cooled and then evaporated to yield the acid chloride which was redissolved in dichloro-methane (200 ml) and added dropwise to a cooled (−5° C.) suspension of 240 g (1,80 mol) aluminum trichloride in 1000 ml dichloromethane. After stirring for 5 minutes a gentle stream of ethane was led through the reaction mixture for 5 hours. The resulting mixture was then cautiously poured in ice and conc hydrochloric acid. After shaking, the layers where separated and the organic layer was washed with 10% sodium carbonate. The solution was dried (magnesium sulfate), filtered and evaporated to yield 140 g of a crude raw product, which was subjected to a silica column and eluted using trimethylpentane/diethyl ether (1:1) as eluant. Yield 80.0 g (75%).: 1H NMR (300 MHz, CDCl13) d 2.53 (t, 2H), 3.05 (t, 2H), 3.55 (s, 2H), 6.90 (m, 2H), 7.1 (m, 1H); 13C NMR (300 MHz, CDCl3) d 28.18 (CH2), 37.57 (CH2), 44.14 (F-coupl, CH2), 44.21 (F-coupl, CH2), 44.28 (F-coupl, CH2), 113.39 (F-coupl, CH), 113.43 (F-coupl, CH), 113.67 (F-coupl, CH), 113.71 (F-coupl, CH), 114.21 (F-coupl, CH), 114.29

(F-coupl, CH), 114.49 (F-coupl, CH), 114.57 (F-coupl, CH), 128.65 (F-coupl, C), 128.69 (F-coupl, C), 129.36 (F-coupl, CH), 129.46 (F-coupl, CH), 138.54 (F-coupl, C), 138.64 (F-coupl, C), 159.85 (C), 163.10 (C), 210.21 (C); MS m/e 164 (M+, 53), 122 (100), 135 (35), 133 (14), 96 (10).

EXAMPLE 24

2-N-n-Propyl-amino-6-fluoro-1,2,3,4-tetrahydronaphthalene

To a solution of 77.5 (0.47 mol) 7-fluoro-1,2,3,4-tetrahydro-2-naphthalenone in 750 ml methanol was 30 ml acetic acid, 30 ml (41.7 g, 0.70 mol)n-propylamine and 60 g (0.93 mol) sodium cyanoborohydride subsequently and portion-wise added. The resulting mixture was stirred for 5 hours and 200 ml 10% hydrochloric acid was thereafter added drop-wise followed by 125 ml water. After stirring over night, the mixture was reduced in volume by evaporation. Diethyl ether, water and 10% sodium carbonate was added until basic reaction occurred. The mixture was shaken and separated and extracted two additional times with diethyl ether. The combined organic extracts where dried (magnesium sulfate), filtered and evaporated to yield 87 g raw product (91%), which was not further purified.: MS m/e 207 (M+, 42), 149 (100), 178 (70), 147 (17), 109 (15).

EXAMPLE 25

2-(N-n-Propylpropionyl)amino-6-fluoro-1,2,3,4-tetrahydronaphthalene

Propionyl chloride (39.4 ml, 37.0 g 0.40 mol) was added drop-wise to a solution of 83.0 g (0.40 mol) 2-N-n-propyl-amino-6-fluoro-1,2,3,4-tetrahydro-naphthalenein 370 ml dichloromethane and 50 ml triethyl amine. The solution was stirred at ambient temperature for 1.5 hours and then washed with 10% sodium carbonate, dried (magnesium sulfate), filtered and evaporated to yield 118.0 g (112%) crude raw product.: MS m/e 263 ((M+, 0.2), 148 (100), 116 (74), 149 (30), 133 (10).

EXAMPLE 26

2-(N-n-Propylpropionyl)amino-6-fluoro-7-nitro-1,2,3,4-tetrahydronaphthalene

To a solution of 30 g (0.11 mol) 2-(N-n-propylpropionyl)amino-6-fluoro-1,2,3,4-tetrahydronaphthalene in 200 ml nitromethane was 40 ml 33% (in concentrated sulfuric acid) nitric acid added dropwise. The mixture was stirred for 30 minutes and then poured on ice and extracted 3 times with diethyl ether. The combined etheric extracts where washed (10% sodium carbonate), dried (magnesium sulfate), filtered and evaporated to yield 14 g of an isomeric mixture. Purification on a silica column using diethyl ether as eluant yielded 2.7 g of a mixture of the two isomers and 4.4 g of pure 2-(N-n-Propyl-propionyl)amino-6-fluoro-7-nitro-1,2,3,4-tetrahydronaphthalene.: 1H NMR (300 MHz, CDCl3) d 0.95 (t, 3H), 1.15 (t, 3H), 1.65 (q, 2H), 2.0 (m, 2H), 2.38 (q, 2H), 2.8–3.1(m, 4H), 3.20 (t, 2H), 4.05 (m, 0.33H), 4.58 (m, 0.67H), 6.99 (d (jFortho=11.1 Hz, 1H), 7.75 (d (jFmeta=6.8 Hz, 1H); MS m/e 308 (M+, 1), 116 (100), 57 (45), 193 (29), 163 (21 ), 86 (16).

EXAMPLE 27

2-(N-n-Propylpropionyl)amino-6-fluoro-7-amino-1,2,3,4-tetrahydronaphthalene

A mixture of 4.40 g (14.3 mmol) 2-(N-n-propylpropionyl)-amino-6-fluoro-7-nitro-1,2,3,4-tetrahydronaphthalene and 0.3 g Pd/C in 200 ml absolute ethanol was hydrogenated in a Parr apparatus for 18 hours. The mixture was filtered (Celite) and evaporated to yield 3.7 g (93%)pure product. To a solution of 3.7 g (13.3 mmol) 2-(N-n=propylpropionyl)-amino-6-fluoro-7-amino-1,2,3,4-tetrahydronaphtalene in 200 ml dry diethyl ether was 1.1 g (29 mmol) litiumaluminum hydride added portion-wise. The mixture was stirred for 2 hours. Water (1.1 ml), 1.1 ml 15% sodium hydroxide and 3.3 ml water was added subsequently. The mixture was stirred for 20 minutes, filtered and evaporated to yield 3.3 (94%) of a pure product: 2-(N-n-Dipropyl)amino-6-fluoro-7-amino-1,2,3,4-tetrahydro-naphtalene. A mixture of 3.0 g (11.3 mmol) 2-(N-n-dipropyl)amino- 6-fluoro-7-amino-1,2, 3,4-tetrahydronaphtalene, 2.04 g (12.3 mmol) chloral hydrate, 2.48 g (35.7 mmol) hydroxylammonium hydrochloride and 12.6 g sodium sulfate in 46 ml distilled water was refluxed for 1.5 hours and then cooled to ambient temperature. Ammonia (5% in water) was added until basic reaction ocurred. The resulting mixture was extracted 3 times with ethyl acetate and the combined organic extracts were dried (magnesium sulfate), filtered and evaporated to a residue of 3.80 g. This material was refrigerated and then subjected to a refrigerated solution of 68 ml concentrated sulfuric acid and 6.8 ml distilled water. The resulting mixture was heated to 80° C. and maintained at that temperature for 45 minutes. After cooling, the mixture was poured on 500 ml ice and subsequently made basic using drop-wise addition of ammonia (32%). A similar workup procedure as above yielded 3.5 g (97%) of the dark red product 4-Fluoro-8-(N,N-dipropylamino)-6,7,8,9-tetrahydro-3H-benz[e]indole-1,2-dione.

A solution of 1.68 g (5.3 mmol) 4-fluoro-8-(N,N-dipropylamino)-6,7,8,9-tetrahydro- 3H-benz[e]indole-1,2-dione in 25 ml dry diethyl ether was added drop-wise to a suspension of 2.0 g (53 mmol) litiumaluminum hydride in 100 ml dry diethyl ether at room temperature. The reaction was allowed to stand for 2.5 hours and 2 ml water, 2 ml 15% sodium hydroxide and 6 ml water was added successively. After stirring for 20 minutes, the inorganic salts were filtered off and the resulting solution was evaporated to yield 1.5 g of a raw product. Subjecting this material to a silica column and eluating it with petroleumether/diethyl ether (1:3) yielded 0.70 g (46%) pure material, 4-Fluoro-N,N-N,N-dipropyl- 6,7,8,9-tetrahydro-3H-benz[e]indole-8-amine: m.p. 112°–115° (Free base).

To a cooled (–5° C.) solution of 50 µl (30.4 mg, 0.20 mmol) phosphorous oxychloride in 3.0 ml dimethylformamide was a solution of 57 mg (0.20 mmol) 4-fluoro-8-(N, N-dipropylamine)-6,7,8,9-tetrahydro-3H-benz[e]indole in 2.5 ml dimethylformamide added. After 15 minutes the resulting mixture was slowly heated to 50° C. and maintained at that temperature for 1 hour and was then allowed to assume ambient temperature overnight. The mixture was poured on ice and basified using 10% sodium hydroxide. After extraction 3 times with ethyl acetate, the organic layers were dried (magnesium sulfate), filtered and evaporated to a residue of 45 mg (71%) of reasonably pure material. Purification on a silica column using methanol as eluant afforded 20 mg pure product: 4-Fluoro-1-formyl-N,N-dipropyl-6,7, 8,9-tetrahydro-3H-benz[e]indole-8-amine.

To an ice-cooled solution of 108 mg (0.37 mmol) 4-fluoro-8-(N,N-dipropylamino)-6,7,8,9-tetrahydro-3H-benz[e]indole in 5 ml acetonitrile was added a solution of 64 µl (72 mg, 0.50 mmol) chlorosulfonyl isocyanate in 0.5 ml acetonitrile in an inert atmosphere (Ar). After stirring the reaction mixture for 20 minutes, 31 µl (33 mg, 0.45 mmol) dimethyl formamide was added. After additional stirring for 1 hour, the mixture was poured in ice and 32% ammonia was added drop-wise until the mixture became basic. Extraction 3 times with dichloromethane and 2 times with ethyl acetate afforded an opalescent organic solution/suspension which was evaporated. The residue was redissolved in methanol, inorganic salts were filtered off and the solution was evaporated again to yield 99 mg (85%) of a reasonably pure material: 1-Cyano-4-fluoro-N,N-dipropyl- 6,7,8,9-tetrahydro-3H-benz[e]indole-8-amine, which was further purified on a silica column using methanol as eluant.

EXAMPLE 28

Preparation of
(+)-2-Cyano-N,N-dipropyl-8-amino-6,7,8,9-tetrahydro-3H-benz[e]indole and analogs thereof Initially, 8-Bromo-2-tetralone was prepared by substituting 2-bromophenylacetylchloride in the procedure described in A. H. Horn, C. J. Grol, D. Dijkstra, A. H. Mulder, J. Med. Chem. 21,825 (1978). Next, 8-bromo-2-tetralone (25 g, 111.1 mmol), S-(−)-alpha-methylbenzylamine (71.5 ml, 5 eq.), acetic acid (80 ml), 4 A molecular sieves (15 ml), THF (125 ml) and methanol (125 ml) were introduced into a flask and cooled to 0°. Sodium cyanoborohydride (1.5 g, 2 eq.) was added in portions over a 15 min period. The slurry was allowed to stir for 3 hr. The slurry was filtered and the solvent reduced to a syrup by evaporation in vacuo. The residue was partitioned between ether and 2N aqueous sodium hydroxide. The ether layer was washed with water (3×) and brine. After drying over anhydrous sodium sulfate the solvent was removed in vacuo. The viscous oil was placed on a flash silica gel column (5 cm×50 cm) and eluted with ethyl acetate/hexane (8%) to separate the higher Rf (+)-diastereomer (solidifies upon standing, 17 g). The solvent was raised to 12% to elute the lower Rf (−)-diastereomer (an oil, 16 g). In this manner the 8-bromo-N-[(S)-alpha-methylbenzyl]-2-aminotetralin was obtained.

Procedure 1: (+)-8-Bromo-N-[(S)-alpha-methylbenzyl]-2-aminotetralin (86.5 g) was dissolved in methylene chloride (600 ml) with triethylamine (40 ml) and cooled to 0°. Propionyl chloride (25 ml) was added and the solution stirred one hr. The reaction was washed with water, 2N aq. hydrochloric acid, water, aq. sodium bicarbonate, and brine, then dried over anhydrous sodium sulfate. Solvent removal in vacuo afforded 100 g of a yellow solid, (+)-8-Bromo-N-[(S)-alpha-methylbenzyl]-propionamid-2-yl-tetralin.

Procedure 2: (+)-8-Bromo-N-[(S)-alpha-methylbenzyl] propionamid-2-yl-tetralin 100 g, 259 mmol) in THF (500 ml) was added to a slurry of LAH (9.8 g) in THF (100 ml). The slurry was refluxed for 3 hr, then cooled. Water (10 ml) was cautiously added, followed by 15% aq. sodium hydroxide (10 ml) and water again (29 ml). The slurry was filtered through diatomaceous earth and the solvent removed in vacuo to afford a viscous oil, (+)-8-Bromo-N-[(S)-alpha-methylbenzyl]-N-propyl-2-aminotetralin. Yield equals 88.6 g.

Procedure 3: (+)-8-Bromo-N-[(S)-alpha-methylbenzyl]-N-propyl-2-aminotetralin (25.8 g, 71.8 mmol) and THF (150 ml) were cooled to −78°. t-Butyllithium (88.7 ml of a 1.7M solution in pentane) was added over 5 minutes. The dark solution was stirred for 5 more minutes then quenched with dimethylformamide (16 ml). The solution was allowed to warm to 0° whereupon it was quenched with water. The reaction was partitioned between ether and water, washing the ether layer with water 4×. The solution was washed with brine and dried over anhydrous sodium sulfate. Solvent removal in vacuo afforded an almost quantitative yield of product, (+)-8-Formyl-N-[(S)-alpha-methylbenzyl]-N-propyl- 2-aminotetralin.

Procedure 4: (+)-8-Formyl-N-[(S)-alpha-methylbenzyl]-N-propyl-2-aminotetralin (32 g, 99.7 mmol), methyl azidoacetate (46 g, 4 eq), ether (50 ml), and methanol (300 ml) were cooled to −5°. Sodium methoxide (91.1 ml, 4 eq, of a 25% w/w solution in methanol) was slowly added. The reaction was allowed to warm slowly in a 25° water bath. After one hour at 25°, the solution was cooled to 0° and saturated aqueous ammonium chloride added. The reaction was rapidly partitioned between ether and 10% aq. sodium carbonate (to neutralize the ammonium chloride). The ether layer was washed with water (5×) and brine. The solution was dried over anhydrous sodium sulfate and stripped of solvent in vacuo to afford a liquid. This was simply filtered through a flash silica gel column (4 cm×50 cm) with ethyl acetate/hexane (15:85). (+)-8-[Methyl (Z)-2-azidopropenoat-3-yl]-N-[(S)-alpha-methylbenzyl]-N-propyl-2-aminotetralin (31.6 g) was obtained as a viscous oil.

Procedure 5: (+)-8-[-Methyl (Z)-2-azidopropenoat-3-yl]-N-[(S)-alpha-methylbenzyl]-N-propyl- 2-aminotetralin (15 g) and toluene (350 ml) were brought to reflux for 1.5 hours. The solution was cooled and stripped of solvent. The residue was crystallized from cyclohexane (10.1 g) to yield (+)-2-Carbomethoxy-N-[(S)-alpha-methylbenzyl]-N-propyl-8-amino-6,7,8,9-tetrahydro-3H-benz[e]indole. M.p. 115°, $[\alpha]^{25}_{589}$=+125° (c=1.92 chloroform). Procedure 6: (+)-2-Carbomethoxy-N-[(S)-alpha-methylbenzyl]-N-propyl-8-amino-6,7,8,9-tetrahydro-3H-benz[e]indole (17.9 g, 45.8 mmol) dissolved in THF (15 ml) was added to a saturated solution of ammonia in methanol (100 ml). This solution was heated in a pressure reactor at 90° for 5 days. The solution was cooled and the solvent removed in vacuo. Flash silica gel chromatography (3 cm×40 cm) with ethyl acetate/hexane afforded a white powder (+)-2-Carbamoyl-N-[(S)-alpha-methylbenzyl]-N-propyl- 5-amino-4,5,6,7-tetrahydro-1H-benz[e]indole (12.4 g, m.p. 235°). The product exhibited a (+) optical rotation in methanol.

Procedure 7: (+)-2-Carbamoyl-N-[(S)-alpha-methylbenzyl]-N-propyl-8-amino-6,7,8,9-tetrahydro-3H-benz[e]indole (12 g), 12N aqueous hydrochloric acid (2.44 ml, 1 eq), 10% palladium/carbon (2.5 g), 20% palladium hydroxide/carbon (0.5 g), water (10 ml), THF (20 ml), and methanol (150 ml) were placed in a Parr bottle and hydrogenated at 50 p.s.i. for 12 hr. Diatomaceous earth was added and the slurry was filtered. Sodium hydroxide (1.05 eq) was added. Most of the solvent was removed in vacuo. Water (100 ml) was added and again most of the solvent was removed in vacuo. This procedure was repeated again, stripping off the water until 250 ml remained. The white powder was filtered and washed with water, then dried in vacuo to afford 8.9 g of (+)-2-Carbamoyl-N-propyl-8-amino-6,7,8,9-tetrahydro-1H-benz[e]indole(m.p.230°). $[\alpha]^{25}_{589}$=+69.4° (c=0.535 methanol).

Procedure 8: (+)-2-Carbamoyl-N-propyl-8-amino-6,7,8, 9-tetrahydro-3H-benz[e]indole (4.3 g) was mixed with sodium carbonate (3 eq), bromopropane (5 eq), and acetonitrile (80 ml) and heated to reflux for 18 hours. The slurry was cooled and poured into methylene chloride and washed with water (2×) and brine. The organic layer was dried over anhydrous sodium sulfate and the solvent removed in vacuo to afford a white solid, (+)-2-Carbamoyl-N,N-dipropyl-8-amino-6,7,8,9-tetrahydro-3H-benz[e]indole, which crystallized from methanol/ether as the hydrochloride salt (m.p. 302°—decomp.). $[\alpha]^{25}_{589}$=+88.9° (c=0.835 methanol).

Procedure 9: (+)-2-Carbamoyl-N,N-dipropyl-8-amino-6,7,8,9-tetrahydro-3H-benz[e]indole (1.5 g) was dissolved in THF (25 ml). Burgess' Reagent (Org. Syn. 56, 40) (2.9 g) was added in portions over a 20 minute period. The reaction was allowed to stir for 3 hours. The reaction was partitioned between 10% aqueous sodium carbonate and ether. The ether layer was washed with water and brine. After drying over anhydrous sodium sulfate the solvent was removed in vacuo to afford a white solid, (+)- 2-Cyano-N,N-dipropyl-8-amino-6,7,8,9-tetrahydro-3H-benz[e]indole(1.4 g, m.p. 134°). $[\alpha]^{25}_{589}$=+99.80° (c=1.50 methanol). The product was crystallized as the hydrochloride salt from methanol/ether (m.p.>275°).

EXAMPLE 29

(+)-2-Carbamoyl-N-cyclopropylmethyl-N-propyl-8-amino-6,7,8,9-tetrahydro- 3H-benz[e]indole Using procedure 8 from Example 28, the title compound was obtained by substituting an appropriate amount of bromomethylcyclopropane for bromopropane. 2.2 Grams of starting material afforded 1.69 g of product. The hydrochloride salt was crystallized form methanol/ether (m.p. 309° decomp.). $[\alpha]^{25}_{589}$=+138.45° (c=0.515 methanol).

EXAMPLE 30

(+)-2-Carbamoyl-N-4-(4,4-dimethylpiperidine-2,6-dione-1-yl)butyl-N-propyl-8-amino-6,7,8,9-tetrahydro-3H-benz[e]indole Using procedure 8 from Example 28, the title compound was obtained by substituting an appropriate amount of 4-(4,4-dimethylpiperidine-2,6-dione-1-yl)-n-butyliodide for bromopropane. 2.2 Grams of starting material afforded 1.59 g of product as an oil. The hydrochloride salt was crystallized from isopropanol/ether (m.p. =211° decomp.). $[\alpha]^{25}_{589}$=+57.78° (c=0.72 methanol).

EXAMPLE 31

(+)-2-Cyano-N-4-(4,4-dimethylpiperidine-2,6-dione-1-yl)butyl-N-propyl-8-amino-6,7,8,9-tetrahydro-3H-benz[e]indole Using procedure 9 from Example 28, the title compound was obtained by substituting the appropriate amount of (+)-2-Carbamoyl-N-4-(4,4-dimethylpiperidine-2,6-dione-1-yl)butyl-N-propyl-8-amino-6,7,8,9-tetrahydro-3H-benz[e] indole in the reaction. 1.53 Grams of starting material afforded 1.12 g of a white foam which was crystallized as the hydrochloride salt from methanol/ether (m.p. =224°). $[\alpha]^{25}_{589}$=+73.9° (c= 0.785 methanol).

EXAMPLE 32

(−)-8-Bromo-N-[(S)-alpha-methylbenzyl]-N-propionamid-2-yl-tetralin

Using procedure 1 from Example 28, the title compound was obtained by substituting (−)-8-bromo-N-[(S)-alpha-methylbenzyl]-2-aminotetralin (the lower Rf diastereomer when eluted on TLC with ethyl acetate/hexane) in the reaction. The product was obtained as a viscous oil.

EXAMPLE 33

(−)-8-Bromo-N-[(S)-alpha-methylbenzyl]-N-propyl-2-aminotetralin

Using procedure 2 from Example 28, the title compound was obtained by substituting (−)-8-bromo-N-[(S)-alpha-methylbenzyl]propionamid-2-yl-tetralin in the reaction. The product was obtained as a viscous oil.

EXAMPLE 34

(−)-8-Formyl-N-[(S)-alpha-methylbenzyl]-N-propyl-2-aminotetralin

Using procedure 3 from Example 28, the title compound was obtained by substituting (−)-8-bromo-N-[(S)-alpha-methylbenzyl]-N-propyl-2-aminotetralin in the reaction. The product was obtained as an oil.

EXAMPLE 35

(−)-8-[Methyl (Z)-2-azidopropenoat-3-yl]-N-[(S)-alpha-methylbenzyl]-N-propyl-2-aminotetralin Using procedure 4 from Example 28, the title compound was obtained by substituting (−)-8-formyl-N-[(S)-alpha-methylbenzyl]-N-propyl-2-aminotetralin in the reaction. The product was obtained as an oil.

EXAMPLE 36

(−)-2-Carbomethoxy-N-[(S)-alpha-methylbenzyl]-N-propyl-8-amino-6,7,8,9-tetrahydro-3H-benz[e]indole Using procedure 5 from Example 28, the title compound was obtained by substituting (−)-8-[methyl (Z)-2-azidopropenoat-3-yl]-N-[(S)-alpha-methylbenzyl]-N-propyl-2-aminotetralin in the reaction. The product was obtained as a white solid which could be recrystallized from cyclohexane (plates, m.p. 122°). $[\alpha]^{25}_{589}$=−168.14° (c =1.13 chloroform).

EXAMPLE 37

(−)-2-Carbamoyl-N-[(S)-alpha-methylbenzyl]-N-propyl-8-amino-6,7,8,9-tetrahydro-3H-benz[e]indole Using procedure 6 from Example 28, the title compound was obtained by substituting (−)-2-carbomethoxy-N-[(S)-alpha-methylbenzyl]-N-propyl-8-amino-6,7,8,9-tetrahydro-3H-benz[e]indole in the reaction. The product was obtained as a white form (m.p. =220°). $[\alpha]^{25}_{589}$=−206.17° (c =0.875 methanol).

EXAMPLE 38

(−)-2-Carbamoyl-N-propyl-8-amino-6,7,8,9-tetrahydro-3H-benz[e]indole

Using procedure 7 from Example 28, the title compound was obtained by substituting (−)-2-carbamoyl-N-[(S)-alpha-methylbenzyl]-N-propyl-8-amino-6,7,8,9-tetrahydro-3H-benz[e]indole in the reaction. The product was obtained as a white solid (m.p. 230°). $[\alpha]^{25}_{589}$=−70.41° (c=0.542 methanol).

EXAMPLE 39

(−)-2-Carbamoyl-N,N-dipropyl-8-amino-6,7,8,9-tetrahydro-3H-benz[e]-indole

Using procedure 8 from Example 28, the title compound was obtained by substituting (−)-2-carbamoyl-N-propyl-8-amino-6,7,8,9-tetrahydro-3H-benz[e]indole in the reaction. The product was obtained as a white solid which was crystallized as the hydrochloride salt from methanol/ether (m.p. 302° decomp.). $[\alpha]^{25}_{589}$=−74.4° (c=0.72 methanol).

EXAMPLE 40

(−)-2-Cyano-N,N-dipropyl-8-amino-6,7,8,9-tetrahydro-3H-benz[e]indole

Using procedure 9 from Example 28, the title compound was obtained by substituting (−)-2-carbamoyl-N,N-dipropyl-8-amino-6,7,8,9-tetrahydro-3H-benz[e]indole in the reaction. The product was obtained as a white solid which was crystallized as the hydrochloride salt from methanol/ether (m.p. 309°). $[\alpha]^{25}_{589}$=−105° (c=0.74 methanol).

EXAMPLE 41

(−)-2-Carbamoyl-N-cyclopropylmethyl-N-propyl-8-amino-6,7,8,9-tetrahydro-3H-benz[e]indole Using procedure 8 from Example 28, the title compound was obtained by substituting (−)-2-carbamoyl-N-propyl-8-amino-6,7,8,9-tetrahydro-3H-benz[e]indole and bromomethylcyclopropane in the reaction. The product was obtained as a white solid which was crystallized as the hydrochloride salt from methanol/ether (m.p. 309° decomp.). $[\alpha]^{25}_{589}$=−130° (c=0.55 methanol).

EXAMPLE 42

(−)-2-Carbamoyl-N-4-(4,4-dimethylpiperidine-2,6-dione-1-yl)butyl-N-propyl-8-amino-6,7,8,9-tetrahydro-3H-benz[e]indole Using procedure 8 from Example 28, the title compound was obtained by substituting (−)-2-carbamoyl-N-propyl-8-amino-6,7,8,9-tetrahydro-3H-benz[e]indole and 4-(4,4-dimethylpiperidine-2,6-dione-1-yl)-n-butyliodide in the reaction. The product was obtained as a foam which was crystallized from isopropanol/ether to afford white crystals (m.p. 199°). $[\alpha]^{25}_{589}$=65.6° (c=0.75 methanol).

EXAMPLE 43

(−)-2-Cyano-N-4-(4,4-dimethylpiperidine-2,6-dione-1-yl)butyl-N-propyl-8-amino-6,7,8,9-tetrahydro-3H-benz[e]indole Using procedure 9 from Example 28, the title compound was obtained by substituting (−)-2-carbamoyl-N-4-(4,4-dimethylpiperidine-2,6-dione-1-yl)butyl -N-propyl-8-amino-6,7,8,9-tetrahydro-3H-benz[e]indole in the reaction. The product was obtained as foam which was crystallized from methanol/ether to afford white crystals (m.p. 225°). $[\alpha]^{25}_{589}$=73.9° (c=1.23 methanol).

EXAMPLE 44

8-Chloro-2-(n-propylbenzoyl)amino-1,2,3,4-tetrahydronaphthalene

To a solution of 53 g (0.23 mol) 8-chloro-2-(n-propyl)amino-1,2,3,4-tetrahydronaphthalene and 50 ml triethylamine in 500 ml dichloromethane was added dropwise 33 ml (40 g, 0.28 mol) benzoylchloride. After stirring over night at room temperature, 10% sodium carbonate was added and the mixture was shaken and separated. The organic phase was dried (magnesium sulphate), filtered and evaporated yielding 72 g (95%) raw product.

EXAMPLE 45

8-Chloro-7-nitro-2-(n-propylbenzoyl)amino-1,2,3,4-tetrahydronaphthalene

Fuming nitric acid (100 ml), 33% in concentrated sulphuric acid was added dropwise to a solution of 72 g (0.22 mol) 8-chloro-2-(n-propylbenzoyl)amino-1,2,3,4-tetrahydronaphthalene in 300 ml nitromethane at 0° C. The mixture was allowed to reach ambient temperature and was stirred over night. After pouring on ice water/diethyl ether the mixture was basified (sodium carbonate solution) and the phases separated. The organic phase was dried (magnesium sulphate), filtered and evaporated to a residue of 65.5 g of an isomeric mixture. Elution of the mixture on a silica column (isooctane/diethyl ether, 1:1 ) gave 19 g of 8-chloro-5-nitro-2-(n-propylbenzoyl)amino-1,2,3,4-tetrahydronaphthalene and 12 g of the desired isomer; 8-chloro-7-nitro-2-(n-propylbenzoyl)-amino-1,2,3,4-tetrahydronaphthalene. MS m/e 372 (M+, 3), 374 (M+ +2, isotope, 1), 105 (100), 164 (72), 77 (35), 134 (16), 165 (9).

EXAMPLE 46

7-Amino-2-(n-propylbenzoyl)amino-1,2,3,4-tetrahydronaphthalene

A mixture of 12 g (32 mmol) 8-chloro-7-nitro-2-(n-propylbenzoyl)amino-1,2,3,4-tetrahydronaphthalene, 25 g ammonium formate and 1.0 g Pd/C (added cautiously under inert atmosphere) was stirred over night. After filtering (Celite) and evaporation the material was brought to suspension in ethyl acetate. Filtering and evaporation yielded 7.8 g (22.7 mmol) of 8-chloro-7-amino-2-(n-propylbenzoyl)amino-1,2,3,4-tetrahydronaphthalene, which was recharged with 50 g ammonium formate, 2 g Pd/C (added cautiously under inert atmosphere) and 200 ml ethanol. The mixture was stirred at room temperature for 4 days. The reaction ceased at about 1/1 ratio (GLC) of product and starting material. The mixture was worked-up as below and recharged with ammonium formate and Pd/C. After stirring for two days the reaction was almost completed. The mixture was filtered (Celite) and evaporated. Ethyl acetate and water where added, the mixture shaken and separated. The organic phase was washed (10% sodium carbonate),dried (magnesium sulfate), filtered and evaporated to yield 5.3 g (54%) crude product which was purified on silica column (dichloromethane/methanol, 19:1) giving 3.9 g product.

EXAMPLE 47

7-Amino-2-(n-propylbenzyl)amino-1,2,3,4-tetrahydronaphthalene

7-Amino-2-(n-propylbenzoyl)amino-1,2,3,4-tetrahydronaphthalene (3.9 g, 12.6 mmol) in 75 ml dry diethyl ether was added to a slurry of 4.0 g (105 mmol) lithium-aluminum hydride in 300 ml diethyl ether. After stirring at room temperature for 45 min water (4 ml), 15% sodium hydroxide (4 ml) and water (12 ml) was added cautiously in successive order. Precipitated inorganic salts which appeared after a few minutes where filtered off and the resulting solution was evaporated to give 3.1 g (84%) pure product.: 1H NMR (300 MHz, CDCl3) d 0.88 (t, 6H), 1.45 (sext, 4H), 1.60 (m, 1H), 2.05 (br. d, 1H), 2.50 (t, 4H), 2.60–2.90 (m, 4H), 2.90–3.05 (m, 1H), 3.50 (br. s, 2H), 3.70 (two d, 2H), 6.40–6.50 (s and d of d, 2H), 6.82 (d, 1H), 7.05–7.45 (m, 5H); MS m/e 294 (M+, 16), 146 (100), 91 (71), 119 (39), 203 (36), 120 (36), 265 ( 34).

EXAMPLE 48

8-(N-propyl-N-benzylamino)-6,7,8,9-tetrahydro-3H-benz[e]indole-1,2-dione.

A mixture 7-amino-2-(n-propylbenzyl)amino-1,2,3,4-tetrahydronaphthalene dihydrochloride (5.75 g, 15.6 mmol), 2.83 g (17.1 mmol) chloral hydrate, 3.44 g (49.5 mmol) and 17.4 g sodium sulfate (anhydrous) in 65 ml water was refluxed for 1 hour. After cooling to room temperature 5% ammonia was added and the mixture was extracted several times (ethyl acetate). The combined organic extracts where dried (magnesium sulfate), filtered and evaporated to a residue which was taken up into 100 ml freezer cold sulfuric acid (90% in water). After stirring at room temperature for 30 minutes, the mixture was heated to 80° C, stirred for 30 minutes and then allowed to slowly reach room temperature. The mixture was poured on ice, basified (ammonia) and extracted several times (ethyl acetate), dried (magnesium sulfate), filtered and evaporated to yield 4.4 g..

EXAMPLE 49:

6,7,8,9-Tetrahydro-N-benzyl-N-n-propyl-8-amino-3H-benz[e]indole 8-(N-Propyl-N-benzylamino)-6,7,8,9-tetrahydro-3H-benz[e]indole-1,2-dione(4.2 g, 12.0 mmol) in dry diethyl ether was added drop-wise to a slurry of 4.0 g (105 mmol) lithium aluminum hydride in 200 ml dry diethyl ether. After stirring in room temperature for 1 hour, 4 ml water, 4 ml 15% sodium hydroxide and 12 ml water was added consecutively. Inorganic material was filtered off after 20 minutes stirring. The resulting solution was evaporated to yield 2.7 g of an isomeric mixture (approx. 70:30 in favor of the desired isomer) which was chromatographed on a silica column (petroleum ether/diethyl ether 2:1 ) to afford 1.3 g of the desired product, 0.5 g isomeric mixture and 0.39 g of its isomer.: 1H NMR (300 MHz, CDCl3) d 0.88 (t, 3H), 1.50 (sext, 2H), 1.72 (oct, 1H), 2.10 (br. d, 1H), 2.57 (oct, 2H), 2.80–3.05 (m, 3H), 3.05–3.20 (m, 2H), 3.75 (two d, 2H), 6.02 (sept, 1H), 6.90 (d, J=j=8.4 Hz, 1H), 7.05–7.35 (m, 6H), 7.42 (d, J=j=6.9 Hz, 1H), 8.10 (br. s, 1H); 13C NMR (300 MHz, CDCl3) d 11.89 (CH3), 21.82 (CH2), 25.78 (CH2), 29.01 (CH2), 30.02 (CH2), 52.04 (CH2), 54.48 (CH 2), 55.90 (CH), 100.40 (CH), 108.63 (CH), 123.23 (CH), 123.53 (CH), 126.43 (CH), 127.00 (C), 127.51 (C), 128.05 (CH), 128.40 (CH), 133.53 (C), 141.56 (C); MS m/e 318 (M+, 17), 170 (100), 143 (60), 91 (50), 289 (30), 168 (26).

EXAMPLE 50

1-Formyl-6,7,8,9-tetrahydro-N-benzyl-N-n-propyl-8-amino-3H-benz[e]indole

To a cooled (−5° C.) solution of 20 υl POCl3 in dimethylformamide was added a solution of 25 mg (0,078 mmol) in 2 ml dimethylformamide. After 10 minutes stirring, the ice-bath was removed and stirring was continued for 30 minutes. The mixture was heated to 50° C. for 1.5 hours and then cooled to ambient temperature. After pouting on ice and basification (5% sodium hydroxide), the mixture was extracted (3×dichloromethane), dried (magnesium sulfate), filtered and evaporated (20 mg). The residue was chromatographed on silica (dichloromethane/methanol, 9:1 ) yielding 17 mg (63% ) of the desired material.: 1H NMR (300 MHz, CDCl13) d 0.95 (t, 3H), 2.52 (sext, 2H), 1.90 (m, 1H), 2.10 (br d, 1H), 2.45 (oct, 2H), 2.8–3.3 (m's, 4H), 3.55 (m, 1H), 3.82 (s, 2H), 7.02 (d, 1H), 7.1–7.4 (m, 5H), 7.44 (d, 1H), 7.94 (d, 1H), 9.0 (br s, 1H), 10.22 (s, 1H); 13C NMR (300 MHz, CDCl3) d 11.86 (CH3), 21.45 (CH2), 25.57 (CH2), 30.41 (CH2), 31.88 (CH2), 52.00 (CH2), 54.54 (CH2), 56.23 (CH), 109.55 (CH), 121.03 (C), 124.38 (C), 125.25 (CH), 126.69 (CH), 128.16 (CH), 128.56 (CH), 129.87 (C), 130.80 (C), 133.78, 135.16 (C), 185.71 (C); MS m/e 346 (M+, 9), 198 (100), 91 (97), 317 (76), 170 (68), 148 (48).

EXAMPLE 51

6,7,8,9-Tetrahydro-N-n-propyl-8-amino-3H-benz[e]indole

A mixture of 6,7,8,9-tetrahydro-N-benzyl-N-n-propyl-8-amino-3H-benz[e]indole (300 mg, 0.94 mmol), 200 mg Pd/C and 500 mg ammonium formate in 20 ml ethanol (99% ) was stirred overnight. After filtration (Celite) the solution was evaporated. Diethyl ether and water was added and shaken. The organic phase was washed (10% sodium carbonate), dried (magnesium sulfate), filtered and evaporated to a residue of 197 mg (97%) of the desired product.: MS m/e 228 (M+, 29), 143 (100), 169 (31), 168 (31) 170 (27), 115 (14), 199 (13), 154 (12).

EXAMPLE 52

6,7,8,9-Tetrahydro-N-(1-propen-3-yl)-N-n-propyl-8-amino-3H-benz[e]indole

To a mixture of 53 mg (0.23 mmol) 6,7,8,9-tetrahydro-N-n-propyl-8-amino-3H-benz[e]indole and 500 mg potassium carbonate in 5 ml acetonitrile was added 31 υl (0.37 mmol) allylbromide. The mixture was stirred overnight and evaporated. Dichloromethane and 10% sodium carbonate was added and the mixture shaken. The organic phase was dried (magnesium sulfate), filtered and evaporated to a residue of 48 mg. This crude material was purified on silica (methanol) to yield 37 mg (60%) pure material.: 1H NMR (300 MHz, CDCl3) d 0.90 (t, 3H), 1.53 (sext, 2H), 1.75 (oct, 1H), 2.1 (br. d, 1H), 2.55 (m, 2H), 2.95 (m, 2H), 3.05–3.40 (m's, 5H), 5.09 (d of d, J=j1 =10.2, j2=1.6 Hz, 1H), 5.24 (d of q, J=j1=17.1, j2=1.5 Hz, 1H), 5.95 (m, 1H), 6.52 (s, 1H), 6.92 (d, J=j=8.2 Hz, 1H), 7.16 (m, 2H), 8.15 (br s, 1H); 13C NMR (300 MHz, CDCl13) d 11.94 (CH3), 21.93 (CH2), 26.07 (CH2), 29.22 (CH2), 29.9 (CH2), 51.99 (CH2), 53.87 (CH2), 56.55 (CH), 100.39 (CH2), 100.44 (CH2), 108.69

(CH), 116.19 (C), 116.24 (C), 123.21 (CH), 123.57 (CH), 126.93 (CH), 127.52 (C), 127.87 (C), 133.56 (C), 137.77 (CH); MS m/e 268 (M+, 6), 143 (100), 170 (97), 168 (46), 239 (34), 124 (30).

EXAMPLE 53

1-Formyl-6,7,8,9-tetrahydro-N-(1-propen-3-yl)-N-n-Propyl-8-amino-3H-benz[e]indole This compound was made from 29 mg (0.11 mmol) 6,7,8,9-tetrahydro-N-( 1-propen-3-yl)-N-n-propyl-8-amino-3H-benz[e]indolein a similar manner as previous formylindoles and gave after evaporation 27 mg and after purification on silica (methanol) 16 mg (50%) of the desired product.: 1H NMR (300 MHz, CDCl13) d 0.90 (t, 3H), 1.55 (sext, 2H), 1.75 (m, 1H), 2.1 (br. d, 1H), 2.60 (t, 2H), 2.95 (m 2H), 3.15 (q, 2H), 3.30 (d, 2H), 3.60 (q, 1H), 5.10 (d of d, J=j1=10.1, j2=1.1 Hz, 1H), 5.24 (d of d, J=j1=17.1, j2=1.4 Hz, 1H), 5.95 (m, 1H), 7.02 (d, J=j=18.3 Hz, 1H), 7.21 (d, J=j=18.3 Hz, 1H), 7.95 (s, 1H), 9.95 (br. s, 1H), 10.20 (s, 1H); 13C NMR (300 MHz, CDCl3) d 11.92 (CH3), 21.55 (CH2), 26.18 (CH2), 30.33 (CH2), 32.04 (CH2), 51.92 (CH2), 53.90 (CH2), 56.66 (CH), 109.71 (CH), 116.65 (CH2), 120.87 (C), 124.44 (C), 125.23 (CH), 129.86 (C), 130.73 (C), 134.60 (CH), 135.39 (C), 137.15 (C), 185.77 (CH); MS m/e 296 (M+, 16), 198 (100), 170 (60), 267 ( 58), 197 (43), 143 (21).

EXAMPLE 54

6,7,8,9-Tetrahydro-N-(cyclopropylcarbonyl)-N-n-Propyl-8-amino-3H-benz[e-]indole

To a solution of 64 mg (0.28 mmol) 6,7,8,9-tetrahydro-N-n-propyl-8-amino- 3H-benz[e]indole in 5 ml dichloromethane was 25 ʋl cyclopropanecarboxylic acid chloride added. After the solution was stirred for 0.5 hours 10% sodium carbonate was added and the mixture was shaken. The organic phase was dried (magnesium sulfate), filtered and evaporated to a residue of 79 mg (95%).: MS m/e 296 (M+, 0.3), 169 (100), 168 (46), 170 (23), 143 (13), 69 (12).

EXAMPLE 55

6,7,8,9-Tetrahydro-N-(cyclopropylmethyl)-N-n-propyl-8-amino-3H-benz[e]indole 6,7,8,9-Tetrahydro N-(cyclopropylformyl)-N-n-propyl-8-amino- 3H-benz[e]indole (79 mg, 0.26 mmol) was dissolved in 10 ml dry diethyl ether and treated with 59 mg (8.1 mmol) lithium aluminum hydride. The mixture was stirred overnight. Water (0.3 ml), 0.3 ml 5% ml sodium hydroxide and 0.9 ml water were added consecutively. After 4 a few minutes inorganic material was filtered off and the solution was evaporated to a residue of 54 mg (74% ) of crude product. Further purification on silica (dichloromethane/methanol, 19:1) yielded 38 mg (52%) pure material.: 13C NMR (300 MHz, CDCl13) d 4.37 (4.61,), 8.82 (11.85, CH2), 20.50 (CH2), 25.50 (CH3), 28.29 (CH2), 28.48 (CH2), 51.96 (CH2), 55.44 (CH2), 57.68 (CH), 100.03 (CH), 109.24 (CH), 122.92 (CH), 123.90 (CH), 126.00 (C), 126.19 (C), 127.31 (C), 133.65 (C),), ); MS m/e 282 (24), 170 (100), 143 (63), 253 (47), 168 (31), 169 (30).

EXAMPLE 56

1-Formyl-6,7,8,9-tetrahydro-N-(cyclopropylmethyl)-N-n-propyl-8-amino-3H-benz[e]indole This compound was made from 17 mg (0.060 mmol) 6,7,8,9-tetrahydro-N-(cyclopropylmethyl)-N-n-propyl-3H-benz[e]indole-8-amine in a similar manner as previous formylindoles and gave after usual work-up and purification on silica (methanol) 7.0 mg (38%) of the desired product.: 1H NMR (300 MHz, CDCl3) d 0.15 (q, 2H), 0.50 (q, 2H), 0.92 (t, 4H), 1.55 (sext, 2H), 1.70 (m, 2H), 2.10 (br d, 1H), 2.55 (m, 2H), 2.65 (t, 2H), 2.90–3.60 (m's, 4H), 7.04 (d, J=j=8.3 Hz, 1H), 7.21 (d, J=j=8.3 Hz, 1H), 7.95 (s, 1H), 9.10 (br s, 1H), 10.25 (s, 1H); 13C NMR (300 MHz, CDCl13) d 4.02 (CH2), 4.27 (CH2), 10.35 (CH), 12.05 (CH3), 21.85 (CH2), 26.26 (CH2), 30.53 (CH2), 32.08 (CH2), 52.32 (CH2), 55.69 (CH2), 56.93 (CH), 109.48 (C), 121.12 (C), 124.50 (CH), 125.29 (CH), 130.17 (C), 130.93 (C), 133.48 (CH), 135.12 (C), 185.70 (CH); MS m/e 310 (M+, 14), 198 (100), 281 (78), 170 (70), 199 (36), 112 (36).

EXAMPLE 57

6,7,8,9-Tetrahydro-N-(thiophene-2-yl-acetyl)-N-n-Propyl-8-amino-3H-benz[e]indole To a solution of 6,7,8,9-tetrahydro-N-n-propyl-8-amino-3H-benz[e]indole(60 mg, 0.26 mmol) and 0.1 ml triethylamine in 5 ml dichloromethane, was added 43 ʋl (56 mg,0.34 mmol) thiophen-2-yl-acetic acid chloride. After stirring overnight, the solution was washed (10% sodium carbonate),dried (magnesium sulfate), filtered and evaporated to yield 92 mg (100%) which was not further purified.

EXAMPLE 58

6,7,8,9-Tetrahydro-N-(1-(thiophene-2-yl)acetyl-N-n-propyl-3H-benz[e]indole-8-amine.

6,7,8,9-tetrahydro-N-(thiophene-2-yl-acetyl)-N-n-propyl-3H-benz[e]indole-8-amine (92 mg, 0.26 mmol) in 15 ml dry diethyl ether was treated with 150 mg (4 mmol) litiumaluminum hydride and stirred overnight. Water (0.15 ml), 0.15 ml 10% sodium hydroxide and 0.45 ml water was added consecutively. The precipitated inorganic material was filtered off and the resulting solution evaporated to a residue of 77 mg (88%) raw product. Further purification on silica (petroleumether/diethyl ether, 3:1) gave 38 mg pure product.

EXAMPLE 59

1-Formyl-6,7,8,9-tetrahydro-N-(1-(thiophene-2-yl)-eth-2-yl)-N-n-propyl-8-amino-3H-benz[e]indole This compound was made from 24 mg (0.071 mmol) 6,7,8,9-tetrahydro-N-(1-(thiophene- 2-yl)-eth-2-yl)-N-n-propyl-8-amino-3H-benz[e]indole in a similar manner as previous formylindoles and gave after evaporation 27 mg and after purification on silica (methanol) 15 mg (58%) of the desired product.: MS m/e 269 (M+–97, 100, M+-thiophenemeth.), 198 (57), 168 (28), 72 (27), 270 (27), 155 (23).

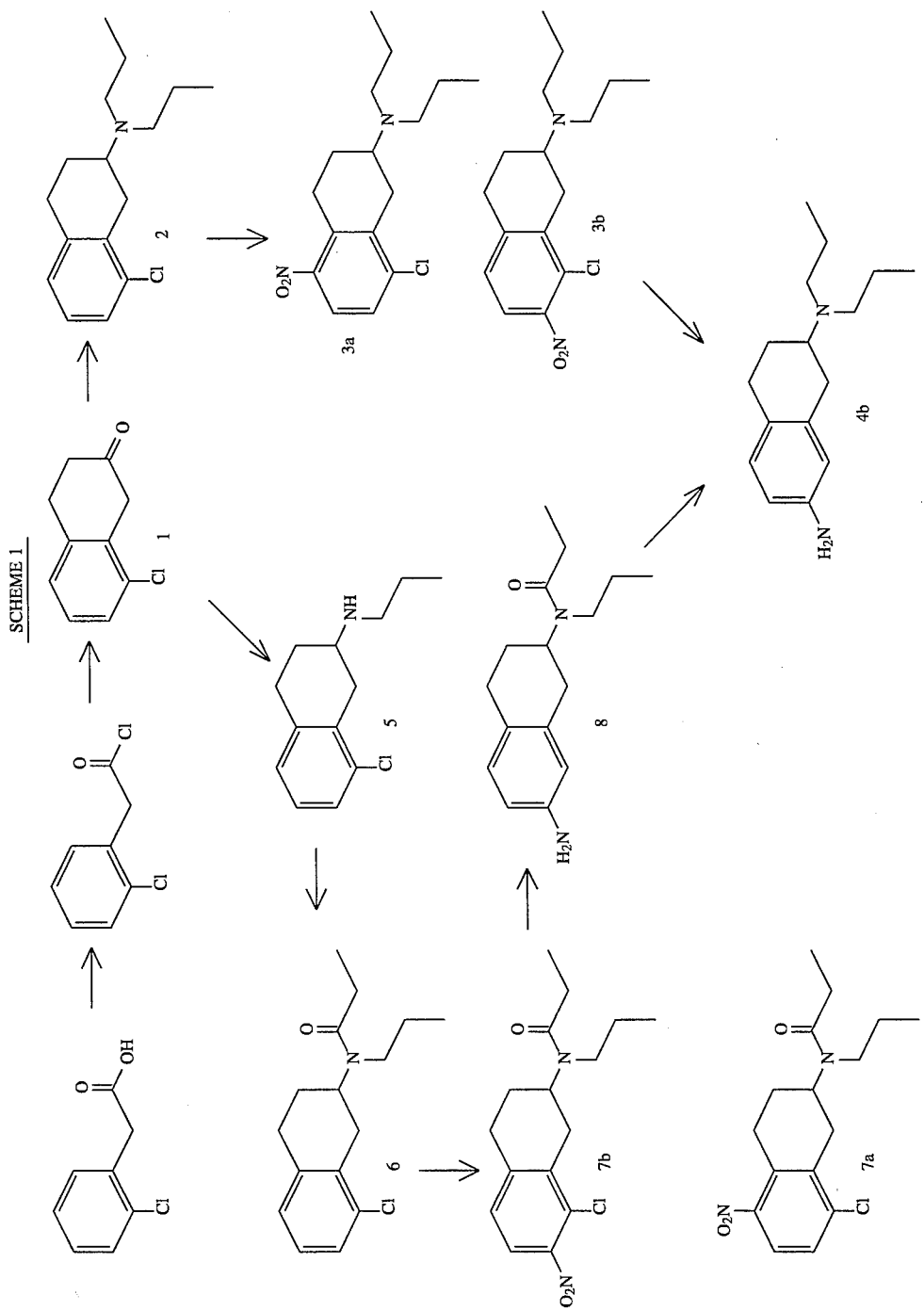
SCHEME 1

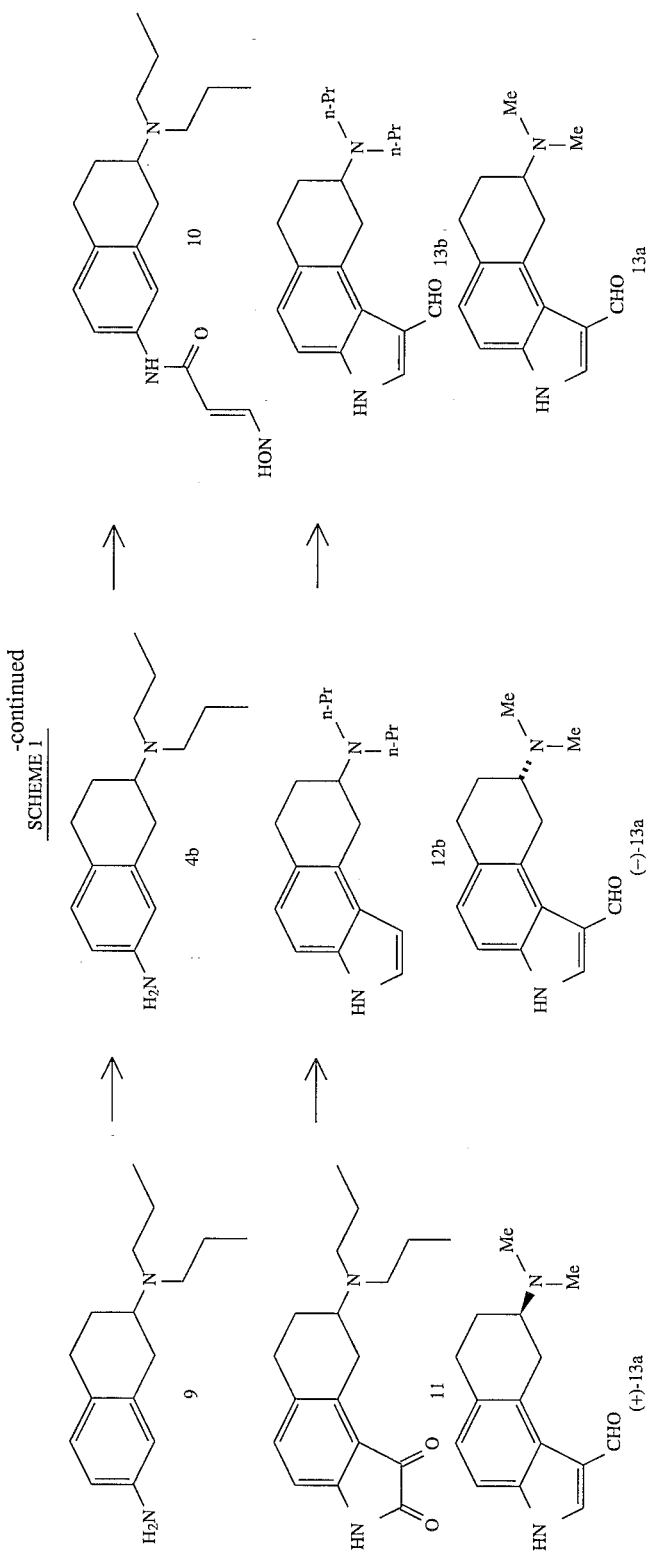

SCHEME 2

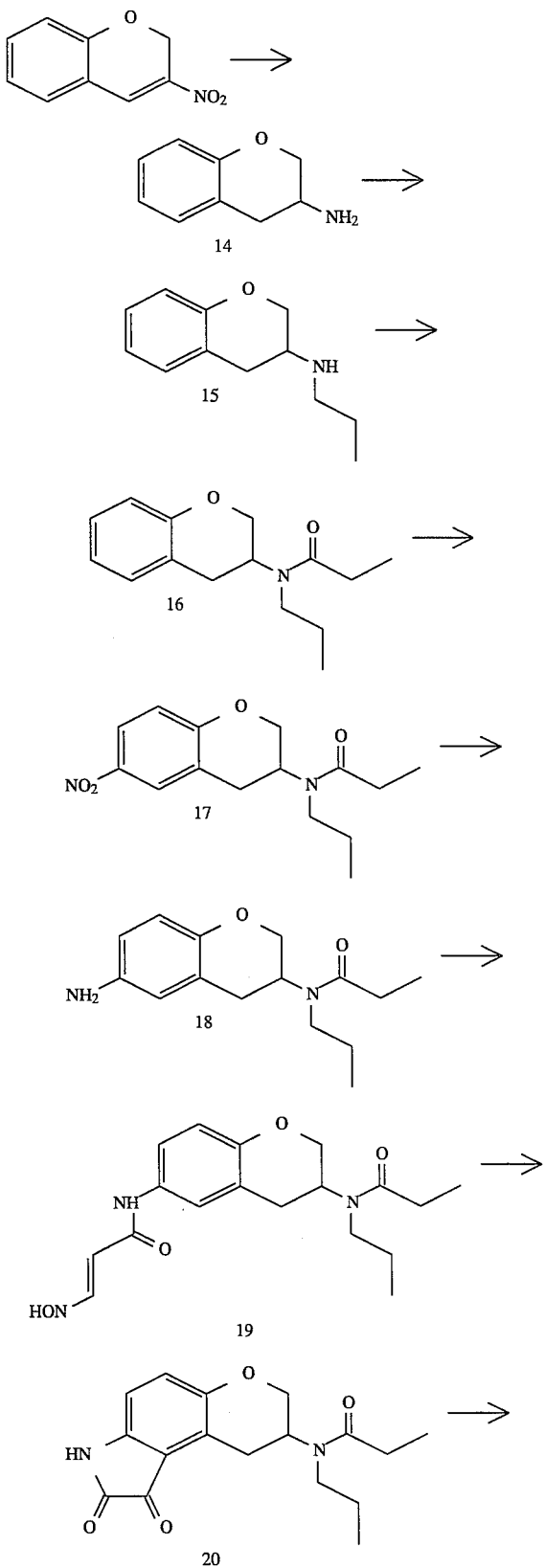

-continued
SCHEME 2

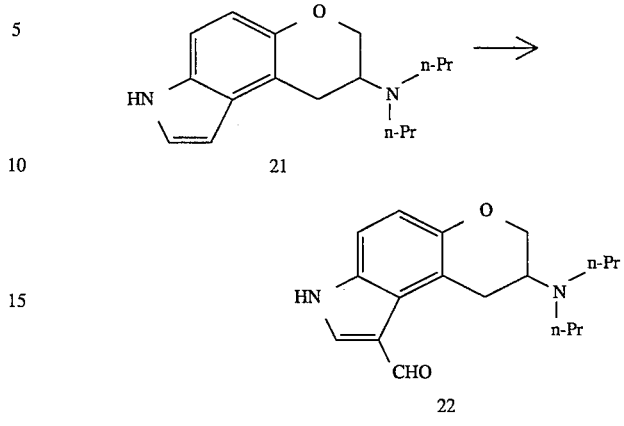

What is claimed:

1. A compound of Formula I:

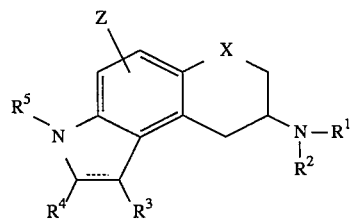

or pharmaceutically acceptable salts thereof wherein $R^1$ is H, $C_1$–$C_3$ alkyl, —$(CH_2)_n CONH_2$ wherein n is 2 to 6, $(CH_2)_n$-1-(4,4-dimethylpiperidine-2,6-dione-yl), or cyclopropylmethyl;

$R^2$ is hydrogen, $C_1$–$C_8$ alkyl, $C_3$–$C_8$ cycloalkyl, $C_2$–$C_8$ alkenyl, $C_2$–$C_8$ alkynyl, $(CH_2)_n$—R"—Ar where R" is O, S, or NH, and Ar is phenyl pyridyl, naphthyl, or indolyl (all of which may be optionally substituted with one or more of $OR^1$, F, Cl, Br, I, CN, CHO, $(CH_2)_m$ phenyl, $NO_2$, $SR^1$, or $NHR^1$) 3,3,3-trifluoropropyl, —$(CH_2)_m$—$R^9$ (where m is 2 or 3 and $R^9$ is phenyl, 2-thienyl or 3-thienyl) or $R^1$ and $R^2$ are taken together to form a hetero- $C_3$–$C_8$ cycloalkyl with said nitrogen atom;

$R^3$ is hydrogen, $C_1$–$C_3$ alkyl, 2,2,2-trifluoroethyl, 3,3,3-trifluoropropyl, formyl, CN, halogen, $CH_2OR^2$, $C(O)C(O)OR^1$, $C(O)CO NR^1R^2$, —$(CH_2)q$ —$NR^1R^2$ where q is 0 to 5, —CH=$NOR^2$, 2(4,5-dihydro)oxazolyl, or $COR^{10}$ where $R^{10}$ is H, $R^1$, $NR^1R^2$ or $CF_3$ $R^4$ is hydrogen, $C_1$–$C_3$ alkyl, cyclopropylmethyl, $CF_3$, 2,2,2-trifluoroethyl, CN, $CONR^1R^2$, =O, 2(4,5-dihydro)imidazolyl, 2(4,5-dihydro)oxazolyl, 2-oxazolyl, 3-oxadiazolyl, or 3,3,3-trifluoropropyl;

$R^5$ is $R^1$, $OCH_3$, $C(O)CH_3$ or $C(O)OR^1$;

X is $NR^5$ where $R^5$ is H, $C_1$–$C_8$ alkyl, $C_3$–$C_8$ cycloalkyl, benzyl, $COR^6$ where $R^6$ is a $C_1$–$C_3$ alkyl, phenyl, or $CONR^7R^8$ where $R^7$ and $R^8$ are independently H or $C_1$–$C_3$ alkyl; and Z is a hydrogen or halogen.

2. The compound of claim 1 where $R^1$ and $R^2$ are independently chosen from a $C_1$–$C_3$ alkyl.

3. The compound of claim 1 where $R^1$ and $R^2$ are both n-propyl.

4. The compound of claim 1 where $R^3$ is formyl.
5. The compound of claim 1 where $R^4$ is hydrogen.
6. The compound of claim 1 where $R^1$ and $R^2$ are independently chosen from a $C_1$–$C_3$ alkyl, $R^3$ is formyl and $R^4$ is hydrogen.
7. The compound of claim 6 where $R^1$ and $R^2$ are both n-propyl.
8. A pharmaceutical composition comprising a pharmaceutically acceptable carrier and an antidepressant therapeutically effective amount of a compound of Formula I

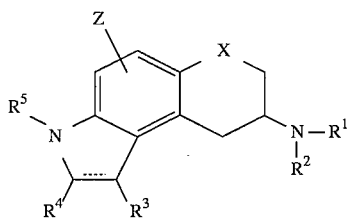

or pharmaceutically acceptable salts thereof wherein $R^1$ is H, $C_1$–$C_3$ alkyl, —$(CH_2)_n CONH_2$ wherein n is 2 to 6, $(CH2)_n$-1-(4,4-dimethylpiperidine-2,6-dione-yl), or cyclopropylmethyl;

$R^2$ is hydrogen, $C_1$–$C_8$ alkyl, $C_3$–$C_8$ cycloalkyl, $C_2$–$C_8$ alkenyl, $C_2$–$C_8$R"-Ar where R" is O, S, or NH, and Ar is phenyl pyridyl, naphthyl, or indolyl (all of which may be optionally substituted with one or more of $OR^1$, F, Cl Br, I, CN, CHO, $(CH_2)_m$ phenyl, $NO_2$, $SR^1$, or $NHR^1$) 3,3,3-trifluoropropyl, —$(CH_2)_m$—$R^9$ (where m is 2 or 3 and $R^9$ is phenyl, 2-thienyl or 3-thienyl) or $R^1$ and $R^2$ are taken together to form a hetero- $C_3$–$C_8$ cycloalkyl with said nitrogen atom;

$R^3$ is hydrogen, $C_1$–$C_3$ alkyl, 2,2,2-trifluoroethyl, 3,3,3-trifluoropropyl, formyl, CN, halogen, $CH_2OR^2$, $C(O)C(O)OR^1$ $C(O)CO$ $NR^1R^2$, —$(CH_2)_q$—$NR^1R^2$ where q is 0 to 5, $CH=NOR^2$, 2(4,5-dihydro)oxazolyl, or $COR^{10}$ where $R^{10}$ is H, $R^1$, $NR^1R^2$ or $CF_3$;

$R^4$ is hydrogen, $C_1$–$C_8$ alkyl, cyclopropylmethyl, $CF_3$, 2,2,2-trifluoroethyl, CN, $CONR^1R^2$, =O, 2(4,5-dihydro)imidazolyl, 2(4,5-dihydro)oxazolyl, 2-oxazolyl, 3-oxadiazolyl, or 3,3,3-trifluoro propyl;

$R^5$ is $R^1$, $OCH_3$, $C(O)CH_3$ or $C(O)OR^1$;

X is $NR^5$ where $R^5$ is H, $C_1$–$C_8$ alkyl, $C_3$–$C_8$ cycloalkyl, benzyl, $COR^6$ where $R^6$ is a $C_1$–$C_3$ alkyl, phenyl, or $CONR^7R^8$ where $R^7$ and $R^8$ are independently H or $C_1$–$C_3$ alkyl; and Z is a hydrogen or halogen.

9. The composition of claim 8 where $R^1$ and $R^2$ are independently chosen from a $C_1$–$C_3$ alkyl, $R^3$ is formyl and $R^4$ is hydrogen.

10. The composition of claim 9 where $R^1$ and $R^2$ are both n-propyl.

11. A method for treating depression comprising administering to a depressed patient a therapeutic amount of a compound of Formula I:

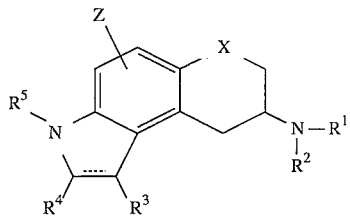

or pharmaceutically acceptable salts thereof wherein $R^1$ is H, $C_1$–$C_3$ alkyl, —$(CH_2)_n CONH_2$ wherein n is 2 to 6, $(CH2)_n$- 1-(4,4-dimethylpiperidine- 2,6-dione-yl), or cyclopropylmethyl;

$R^2$ is hydrogen, $C_1$–$C_8$ alkyl, $C_3$–$C_8$ cycloalkyl, $C_2$–$C_8$ alkenyl, $C_2$–$C_8$alkynyl, $(CH_2)_n$—R"—Ar where R"is O, S, or NH, and Ar is phenyl pyridyl, naphthyl, or indolyl (all of which may be optionally substituted with one or more of $OR^1$, F, Cl, Br, I, CN, CHO, $(CH_2)_m$ phenyl, $NO_2$, $SR^1$, or $NHR^1$) 3,3,3-trifluoropropyl, —$(CH_2)_m$—$R^9$ (where m is 2 or 3 and $R^9$ is phenyl, 2-thienyl or 3-thienyl) or $R^1$ and $R^2$ are taken together to form a hetero- $C_3$–$C_8$ cycloalkyl with said nitrogen atom;

$R^3$ is hydrogen, $C_1$–$C_3$ alkyl, 2,2,2-trifluoroethyl, 3,3,3-trifluoropropyl, formyl, CN, halogen, $CH_2OR^2$, $C(O)C(O)OR^1$ $C(O)CO$ $NR^1R^2$, —$(CH_2)_q$—$NR^1R^2$ where q is 0 to 5, —$CH=NOR^2$, 2(4,5-dihydro)oxazolyl, or $COR^{10}$ where $R^{10}$ is H, $R^1$, $NR^1$, $R^2$ or $CF_3$;

$R^4$ is hydrogen, $C_1$–$C_3$ alkyl, cyclopropylmethyl, $CF_3$, 2,2,2-trifluoroethyl, CN, $CONR^1R^2$, =O, 2(4,5-dihydro)imidazolyl, 2(4,5-dihydro)oxazolyl, 2-oxazolyl, 3-oxadiazolyl, or 3,3,3-trifluoropropyl;

$R^5$ is $R^1$, $OCH_3$, $C(O)CH_3$ or $C(O)OR^1$;

X is $NR^5$ where $R^5$ is H, $C_1$–$C_8$ alkyl, $C_3$–$C_8$ cycloalkyl, benzyl, $COR^6$ where $R^6$ is a $C_1$–$C_3$ alkyl, phenyl, or $CONR^7R^8$ where $R^7$ and $R^8$ are independently H or $C_1$–$C_3$ alkyl; and Z is a hydrogen or halogen.

12. The method of claim 11 wherein said compound is administered in an amount of from about 1 to about 2000 mg oral daily dose, or from about 0.1 to about 100 mg parenteral daily dose.

* * * * *